US010139282B2

(12) United States Patent
Chrostowski

(10) Patent No.: US 10,139,282 B2
(45) Date of Patent: Nov. 27, 2018

(54) THERMAL IMAGING SYSTEM

(71) Applicant: Scott Technologies, Inc., Boca Raton, FL (US)

(72) Inventor: Andrew Chrostowski, Monroe, NC (US)

(73) Assignee: Scott Technologies, Inc., Monroe, NC (US)

( * ) Notice: Subject to any disclaimer, the term of this patent is extended or adjusted under 35 U.S.C. 154(b) by 0 days.

(21) Appl. No.: 15/567,680

(22) PCT Filed: Apr. 22, 2016

(86) PCT No.: PCT/US2016/028828
§ 371 (c)(1),
(2) Date: Oct. 19, 2017

(87) PCT Pub. No.: WO2016/172469
PCT Pub. Date: Oct. 27, 2016

(65) Prior Publication Data
US 2018/0156667 A1 Jun. 7, 2018

Related U.S. Application Data

(60) Provisional application No. 62/151,080, filed on Apr. 22, 2015, provisional application No. 62/208,155, filed on Aug. 21, 2015.

(51) Int. Cl.
*G01J 5/02* (2006.01)
*H04N 5/33* (2006.01)
(Continued)

(52) U.S. Cl.
CPC ............ *G01J 5/025* (2013.01); *A61B 5/0017* (2013.01); *A61B 5/0022* (2013.01);
(Continued)

(58) Field of Classification Search
CPC .... G01N 21/84; G01N 33/00; G01N 33/0031; G01J 1/0437; G01J 1/42; G08B 13/02;
(Continued)

(56) References Cited

U.S. PATENT DOCUMENTS 6,069,557 A 5/2000 Anglin, Jr. et al.
6,310,552 B1 10/2001 Stumberg et al.
(Continued)

OTHER PUBLICATIONS

International Search Report and Written Opinion of the International Searching Authority dated Sep. 1, 2016 issued in corresponding PCT Application Serial No. PCT/US2016/028828, consisting of 5-pages.

(Continued)

*Primary Examiner* — Kiho Kim

(57) ABSTRACT

A thermal imaging system includes an infrared (IR) detector configured to detect ambient IR radiation in a surrounding environment of the IR detector and pulse sequences of mechanically-generated IR radiation in a status message emitted by a portable signaling device mounted on a wearer. The status message represents an operating status of the wearer and a processor operably connected to the IR detector analyzes the pulse sequences in the status message and generates a display message based on the pulse sequences. The display message is display on a screen for viewing by an operator of the thermal imaging system. The display message is presented as visual indicia representative of the operating status of the wearer which is displayed concurrently with a graphical image of the surrounding environment that is based on the ambient IR radiation detected by the IR detector.

20 Claims, 9 Drawing Sheets

(51) Int. Cl.

| | |
|---|---|
| *H04N 5/225* | (2006.01) |
| *A61B 5/00* | (2006.01) |
| *A61B 5/01* | (2006.01) |
| *A61B 5/0205* | (2006.01) |
| *A61B 5/11* | (2006.01) |
| *A61B 5/117* | (2016.01) |
| *G08B 21/04* | (2006.01) |
| *G08B 25/01* | (2006.01) |
| *G08B 27/00* | (2006.01) |
| *A62B 9/00* | (2006.01) |
| *G01K 13/02* | (2006.01) |
| *G01L 19/12* | (2006.01) |
| *G01P 13/00* | (2006.01) |
| *G08B 23/00* | (2006.01) |
| *G16H 40/67* | (2018.01) |
| *G06F 19/00* | (2018.01) |
| *G01J 5/00* | (2006.01) |
| *A61B 5/024* | (2006.01) |
| *H04N 5/232* | (2006.01) |

(52) U.S. Cl.
CPC .......... *A61B 5/0024* (2013.01); *A61B 5/0059* (2013.01); *A61B 5/0075* (2013.01); *A61B 5/01* (2013.01); *A61B 5/015* (2013.01); *A61B 5/02055* (2013.01); *A61B 5/117* (2013.01); *A61B 5/1123* (2013.01); *A61B 5/742* (2013.01); *A61B 5/747* (2013.01); *A62B 9/006* (2013.01); *G01K 13/02* (2013.01); *G01L 19/12* (2013.01); *G01P 13/00* (2013.01); *G06F 19/00* (2013.01); *G08B 21/0415* (2013.01); *G08B 21/0453* (2013.01); *G08B 21/0476* (2013.01); *G08B 23/00* (2013.01); *G08B 25/016* (2013.01); *G08B 27/001* (2013.01); *G16H 40/67* (2018.01); *H04N 5/2252* (2013.01); *H04N 5/2256* (2013.01); *H04N 5/33* (2013.01); *H04N 5/332* (2013.01); *A61B 5/02438* (2013.01); *A61B 5/11* (2013.01); *A61B 5/6803* (2013.01); *A61B 5/6804* (2013.01); *A61B 5/6823* (2013.01); *A61B 2503/20* (2013.01); *A61B 2560/0242* (2013.01); *G01J 2005/0077* (2013.01); *G01K 2013/024* (2013.01); *H04N 5/23293* (2013.01)

(58) Field of Classification Search
CPC ...... G08B 21/18; G08B 17/10; G08B 29/181; G08B 3/00; G08B 3/10; G08B 19/005; G08B 21/12; G08B 17/113; H01R 13/6205; H01R 13/627; G01F 1/00; G01D 7/00; G01D 11/245
See application file for complete search history.

(56) References Cited

U.S. PATENT DOCUMENTS

| | | | |
|---|---|---|---|
| 7,377,835 B2 | 5/2008 | Parkulo et al. | |
| 2005/0224716 A1 | 10/2005 | Armentrout et al. | |
| 2008/0214219 A1* | 9/2008 | Matsushima | ........ A61B 5/0002 455/500 |
| 2015/0022356 A1* | 1/2015 | Gettings | ................ G01N 21/84 340/568.1 |

OTHER PUBLICATIONS

International Search Report and Written Opinion of the International Searching Authority dated Sep. 1, 2016 issued in corresponding PCT Application Serial No. PCT/US2016/028592, consisting of 6-pages.

* cited by examiner

THERMAL IMAGING SYSTEM

CROSS-REFERENCE TO RELATED APPLICATIONS

This application is a Submission Under 35 U.S.C. § 371 for U.S. National Stage Patent Application of International Application No.: PCT/US2016/028828, filed Apr. 22, 2016 entitled "THERMAL IMAGING SYSTEM," which claims priority to U.S. Provisional Application No. 62/151,080, filed Apr. 22, 2015, entitled "THERMAL IMAGING SYSTEM" and U.S. Provisional Application No. 62/208,155, filed Aug. 21, 2015, entitled "THERMAL IMAGING SYSTEM", the entirety of all of which are incorporated herein by reference.

BACKGROUND OF THE INVENTION

The subject matter disclosed herein relates generally to thermal imaging systems that provide thermal signaling to communicate messages. The thermal imaging systems may be used in visually obscured environments, such as by first responders in a smoke filled building.

First responders, such as firefighters, are often relied upon to extinguish fires in buildings or other structures. Additionally, the firefighters are relied upon to rescue persons within the buildings. However, fires typically generate smoke that reduces the visibility within the building and therefore also may reduce the ability of the firefighters to navigate within the building for such tasks as extinguish the fire, rescue persons trapped within the building and/or safe transit into and out of a building.

Accordingly, thermal imaging cameras are gaining use, particularly by the firefighting community for use within buildings that are experiencing reduced visibility caused by, for example, smoke. In operation, thermal imaging cameras enable the firefighters to operate in various environments in which the vision of the firefighter may be obscured because of smoke and/or other materials entrained in the air. Thermal imaging cameras operate in the infrared light spectrum and therefore provide an alternative view to firefighters by enabling the firefighters to "see" in the reduced visibility environment. More specifically, temperature differences between various objects in the building are highlighted and transformed into a visible image on a display that forms part of the thermal imaging camera. The visible images enable the firefighters to navigate throughout the building. The visible images also enable the firefighters to locate a prone or injured person within the building. Thermal imaging cameras further enable a firefighter to locate a "hot spot" that may be obscured by walls or furniture so that an extinguishing agent may be utilized to eliminate the hot spot.

However, known thermal imaging cameras do not enable the firefighter operating the thermal imaging cameras to identify and distinguish individual firefighters. For example, firefighters typically enter a burning building in groups or teams of multiple members. In known thermal imaging cameras, the thermal images may show multiple firefighters of a team, but it is difficult to identify and distinguish between the firefighters in the image. Such information may be useful for determining if any firefighter is unaccounted for, and, if so, which firefighter(s) are unaccounted. Additionally, known thermal imaging cameras do not enable the firefighter operating the camera to receive operational statuses or other helpful information about the firefighters in addition to the thermal images of the environment. For example, using a typical thermal imaging camera, an operator would not be able to ascertain a status of the firefighters being observed, such as whether any of the firefighters have low air pressure in a respective breathing apparatus or whether a stationary firefighter is voluntarily stationary or is incapacitated.

BRIEF DESCRIPTION OF THE INVENTION

A thermal imaging system comprises an infrared (IR) detector configured to detect ambient IR radiation in a surrounding environment of the IR detector. The IR detector is further configured to detect pulse sequences of mechanically-generated IR radiation in a status message emitted by a portable signaling device mounted on a wearer in or around the surrounding environment. The status message represents an operating status of the wearer and one or more processors operably connected to the IR detector. The one or more processors are configured to analyze the one or more pulse sequences in the status message and generate a display message based on the one or more pulse sequences. The one or more processors are configured to convey the display message to a display screen that presents the display message for viewing by an operator of the thermal imaging system. The display message is presented as visual indicia representative of the operating status of the wearer. The visual indicia is displayed concurrently with a graphical image of the surrounding environment that is based on the ambient IR radiation detected by the IR detector.

DETAILED DESCRIPTION OF THE INVENTION

Figure 1:
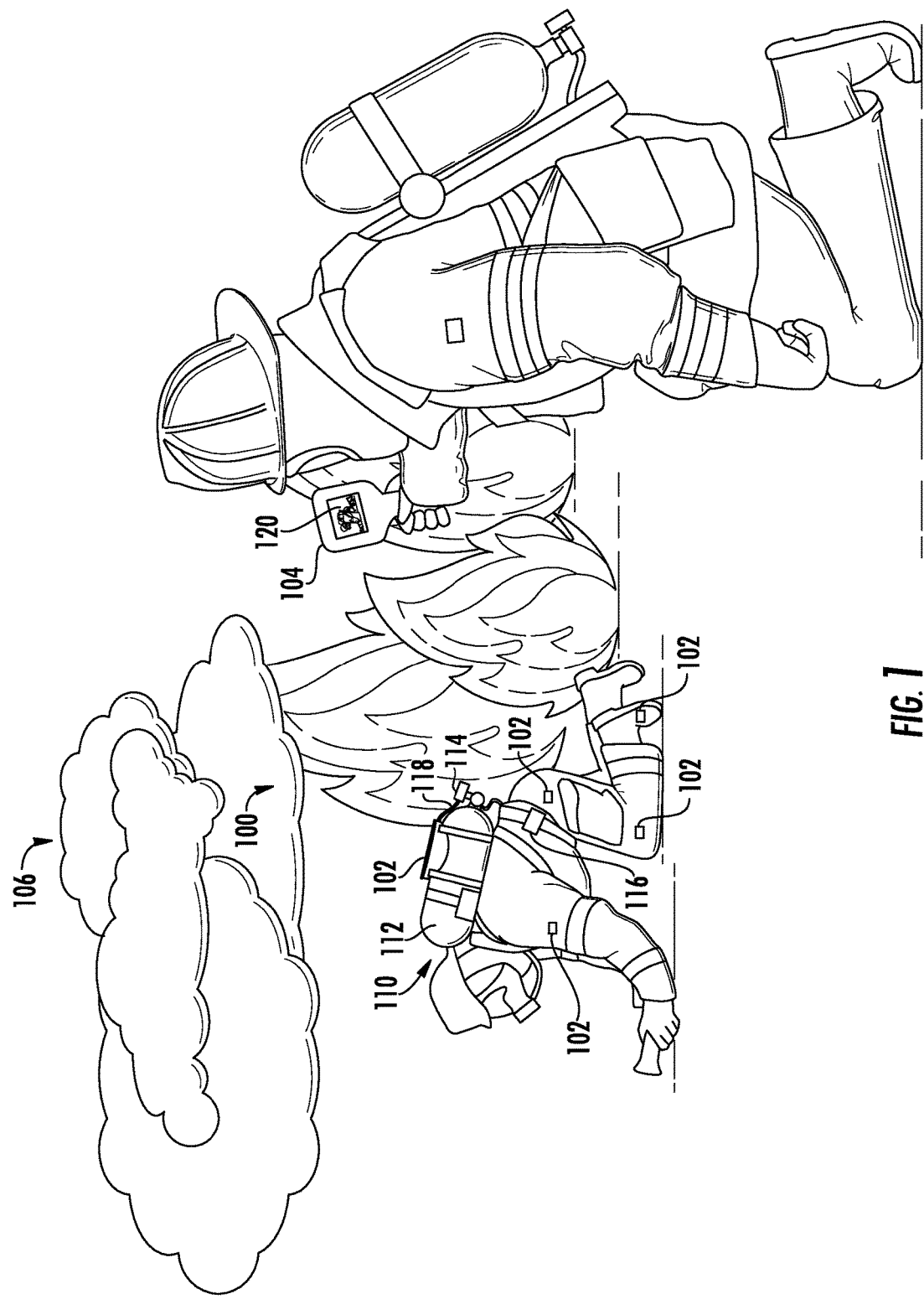
FIG. 1 illustrates a thermal imaging system according to an embodiment being used by two first responders in a low visibility environment.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide thermal imaging systems for signaling in an environment where visible light may be unavailable or absent. For example, one such environment includes a building or structure containing smoke and/or other materials entrained in the air, which may substantially obscure the vision of a person. In another example, an environment may be a building or a lot outside of a building at night when it is dark with little or no lights in the area. More specifically, the various systems described herein provide a portable signaling device that emits infrared (IR) signals that may be detected by a thermal imaging receiver, such as a thermal imaging camera, in a low visibility environment. As used herein, a low visibility environment is an environment which restricts the ability of a firefighter to perform necessary or desirable activities such as visual communications, safe transit, and/or the like, in that environment due to a lack of visible light, smoke interference, or other visual hindrances to the human eye. As used herein, visible light is a range of electromagnetic radiation that can be detected by the human eye. The wavelengths associated with the visible light range are approximately 380 nanometers (nm) to approximately 750 nm. It is recognized that although the various systems and apparatuses described herein may be useful in low visibility environments, the various systems and apparatuses also may be useful in environments with higher visibility. Thus, the various systems and apparatuses described herein are not limited to use in low visibility environments.

Figure 9:
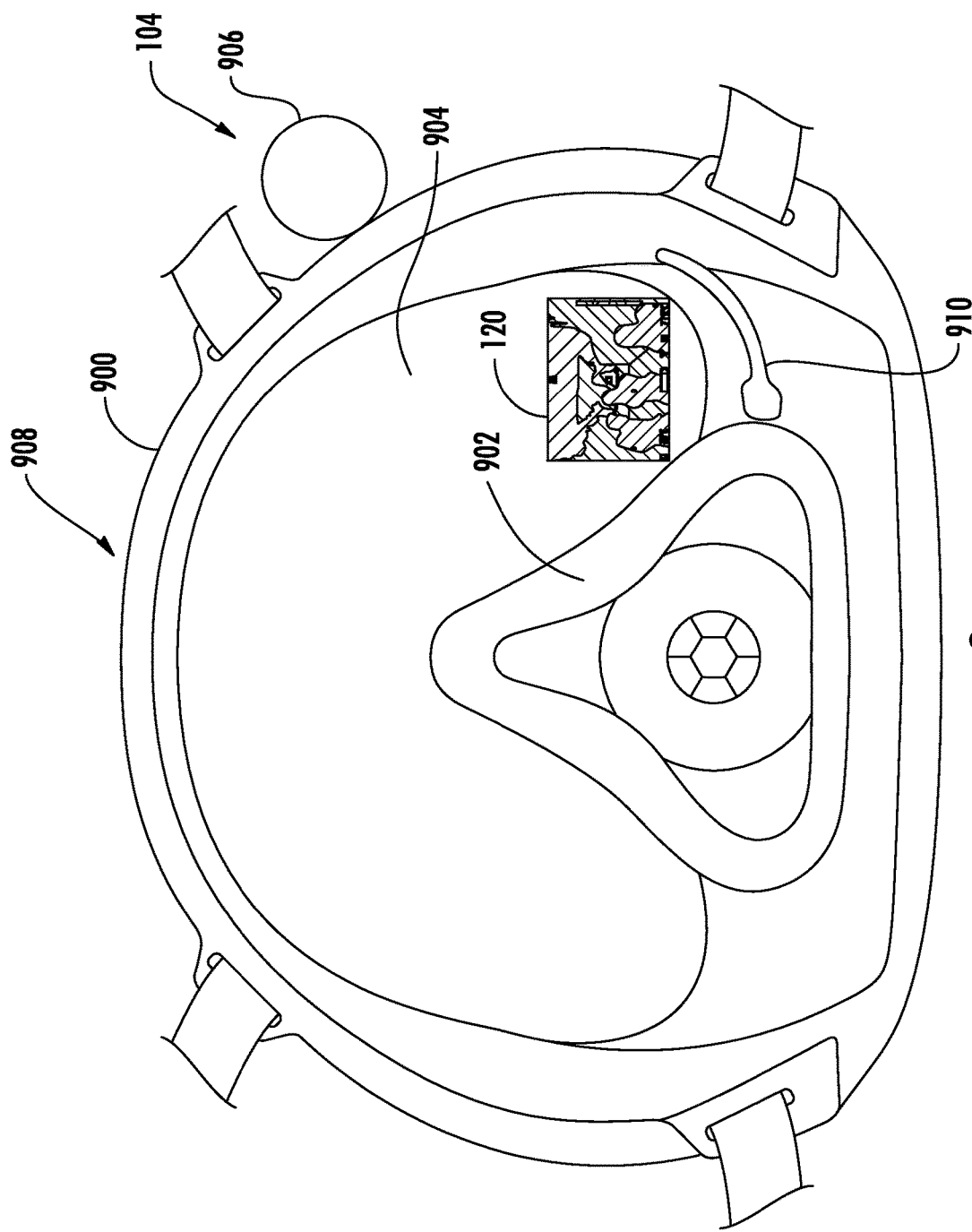
FIG. 9 illustrates an interior view of a mask configured to be worn by a first responder that includes a thermal imaging camera mounted thereon.

FIG. 1 illustrates a thermal imaging system 100 according to an embodiment being used by two first responders in a low visibility environment 106. The thermal imaging system 100 includes a portable signaling device 102 and a thermal imaging camera 104. The portable signaling device 102 is being worn by a first of the two first responders, referred to herein as a wearer. The thermal imaging camera 104 is being held by a second of the two first responders, referred to herein as an operator. In the illustrated embodiment, the low visibility environment 106 is a burning building with smoke entrained in the air. The wearer of the portable signaling device 102 is crawling into and/or through the burning building. The operator holding the thermal imaging camera 104 is rearward of the wearer, and is pointing the thermal imaging camera 104 in the general direction of the wearer. Although only one wearer is shown in FIG. 1, additional wearers (for example, other first responders that are also wearing portable signaling devices 102) may be located in the low visibility environment 106 proximate to the one wearer. Furthermore, although the operator carrying the thermal imaging camera 104 is shown without a signaling device 102, the operator may also carry a signaling device 102. Similarly, the wearer may also carry a thermal imaging camera 104 in addition the signaling device 102 shown in FIG. 1. The thermal imaging camera 104 shown in FIG. 1 is a handheld device, but in an alternative embodiment the thermal imaging camera 104 may be a body-mountable device that is attached to the clothing and/or equipment of the operator. For example, the thermal imaging camera 104 may be mounted on the helmet and/or mask of the operator, as shown in FIG. 9.

The signaling device 102 is configured to emit infrared (IR) signals, which are pulses of IR radiation. The signaling device 102 emits the IR signals in one or more pulse sequences to form a message that is communicated via IR radiation. In an embodiment, the IR signals emitted by the signaling device 102 are detectable by the thermal imaging camera 104. Each pulse sequence includes a series of pulsed IR signals emitted by the signaling device 102. In various embodiments, the message communicated to the thermal imaging camera 104 provides status information about the wearer, and is referred to as a status message. For example, the status message may represent an operating status associated with the wearer of the signaling device 102. The operating status may include various information, such as a health condition of the wearer, an equipment condition of equipment being worn or carried by the wearer, a movement status of the wearer, a location of the wearer, an orientation of the wearer, and/or an identification of the wearer. As described herein in more detail, the health condition of the wearer may include an alarm status of the wearer, (e.g., whether the wearer is in a pre-alarm state, an alarm state, or a non-alarm state), biometric data (e.g., a heart rate of the wearer), a temperature of the air immediately surrounding the wearer, and the like. The equipment condition may indicate wear and/or supply conditions and operating conditions of the equipment (e.g., a quantity of air remaining in an air supply tank 112 carried by the wearer). The movement status of the wearer may indicate if and how the wearer is moving (e.g., moving the left, walking, crawling, stationary, etc.). The location of the wearer may indicate a region of the building that the wearer is located (e.g., kitchen or bathroom), global positional coordinates of the wearer, or a relative location of the wearer relative to the operator (e.g., 50 feet ahead). The orientation of the wearer may indicate whether the wearer is standing upright, in a crawling position, or in lying down position. The orientation information may also indicate whether the wearer is facing towards the thermal imaging camera 104 or away from the camera 104, and whether the wearer lying down is in the chest-down, prone position or the back-down, supine position, which may indicate that the wearer is incapacitated. The identification of the wearer indicates the name of the wearer, the association of the wearer (e.g., team or group), and/or the identity of one or more portable signaling devices emitting the detected IR signals.

The signaling device 102 may be communicatively coupled to a monitoring system 108 (shown in FIG. 5) worn by the wearer. The monitoring system 108 includes one or more controllers and sensors that monitor operating parameters of the wearer and/or the equipment carried by the wearer. For example, the wearer may carry a self-contained breathing apparatus (SCBA) 110 that is worn on the back of the wearer and includes the air supply tank 112. The monitoring system 108 may include a pressure sensor 114 affixed to the SCBA 110 that is configured to monitor a pressure of air within the air supply tank 112 in order to determine how much air remains in the tank 112. The monitoring system 108 may also include a motion sensor 116, such as an accelerometer, that is configured to monitor movement of the wearer, and a temperature sensor 158 (shown in FIG. 5) that is configured to monitor the temperature of the air immediately surrounding the wearer. Data parameters from the pressure sensor 114, the motion sensor 116, the temperature sensor 158, and other sensors in the monitoring system 108 may be electrically conveyed to a controller (e.g., the control circuit 134 shown in FIG. 3) of the signaling device 102 for processing. The controller may be configured to generate the status message based on the input received from the sensors. Optionally, the signaling device 102 may generate the status message based at least in part on input received from the wearer using a user input device, such as a button or toggle device worn by the wearer that allows the wearer to send out a distress or warning message. The signaling device 102 conveys the status message using an IR emitter 132 (shown in FIG. 3). Thus, the operating status associated with the wearer that is communicated in the IR status message to the thermal imaging camera 104 may include one or more data parameters that were measured, determined, or otherwise monitored by the monitoring system 108.

One signaling device 102 shown in FIG. 1 is removably fastened to the SCBA 110 of the wearer. More specifically, the signaling device 102 is fastened to the air supply tank 112. In the illustrated embodiment, the wearer includes multiple signaling devices 102 mounted to the clothing and equipment of the wearer at different locations along the body of the wearer. For example, the signaling device 102 shown on the air supply tank 112 may be a first signaling device 102, and the wearer may additionally carry a second signaling device 102 on the arm of the wearer, a third signaling device 102 along the hip of the wearer, a fourth signaling device 102 along the knee of the wearer, and a fifth signaling device 102 along the boot of the wearer. In an embodiment, all of the signaling devices 102 are configured to emit status message in the form of IR pulses. Although not shown, signaling devices 102 may be disposed at other locations along the body of the wearer, such as at the heel of the boot of the wearer, on the top, front, and/or rear of the helmet, on the chest of the wearer, or the like. The status messages emitted from different signaling devices 102 may be the same or at least similar to one another. For example, the only difference between status messages emitted from two different signaling devices 102 on the wearer may be an identification of the transmitting signaling device 102 and/or a location of the transmitting signaling device 102 relative to the body of the wearer. Thus, one status message may indicate that the message is transmitted from the signaling device 102 on the boot of the wearer, while another status message may indicate that the message is transmitted from the signaling device 102 on the arm of the wearer.

In an embodiment, the wearer may have multiple signaling devices 102 mounted to the wearer in order to transmit status messages in different directions and increase the likelihood that the thermal imaging camera 104 is able to receive at least one of the status messages regardless of the orientation of the wearer. The wearer may carry signaling devices 102 along the sides of the wearer, along the front of the wearer, along the back of the wearer, along the head of the wearer, and/or along the feet of the wearer, such that status messages may be transmitted generally frontward, rearward, and/or sideways from the wearer. The signaling devices 102 may be placed in operationally significant places along the person of the wearer. For example, in order to receive a status message from the wearer when the wearer is crawling away from the operator holding the thermal imaging camera 104, one or more signaling devices 102 may be disposed at the heel of the boot, at the bottom of the air supply tank 112, or the like. Furthermore, another signaling device 102 may be mounted on the top of the helmet of the wearer to be able to receive a status message from the wearer as the wearer crawls, crouches, and/or otherwise moves towards the operator with a lowered head. The signaling devices 102 may be located in places that are operationally significant in both normal situations as well as in emergency situations. For example, a signaling device 102 may be located on the chest of the wearer for the thermal imaging camera 104 to be able to receive a status message in an emergency situation in which the wearer is incapacitated and lying generally on his or her back.

In one or more embodiments, the thermal imaging camera 104 is configured to receive the status message emitted by the one or more signaling devices 102 and is configured to analyze the one or more pulse sequences of IR radiation. The thermal imaging camera 104 is further configured to generate a display message that presents visual indicia (shown in FIG. 8) on a display screen 120 of the thermal imaging camera 104 that is viewable by the operator. The visual indicia represents the operating status associated with the wearer, such that the display screen 120 presents the operating status of the wearer to the operator. The thermal imaging camera 104 is also configured to display a graphical thermal image of the surrounding environment on the display screen 120. The characteristics of the graphical thermal image are based on naturally-occurring or ambient IR radiation emitted by the environment, such as body heat emitted from the wearer in the environment and radiation emitted from walls that are heated from a fire. The thermal imaging camera 104 may display the shape or outline of the wearer on the thermal image in addition to the visual indicia indicative of the operating status of the wearer. Thus, in addition to being able to view the wearer in the environment, the operator is provided additional status information about the wearer, such as the identity of the wearer, a health condition of the wearer, a condition of the equipment worn by the wearer, a location of the wearer, an orientation of the wearer, and/or movement characteristics of the wearer. Although the thermal imaging camera 104 is configured to be handheld by the operator in the embodiment shown in FIG. 1, in an alternative embodiment the thermal imaging camera 104 may be coupled to equipment worn by the operator, such as to the helmet and/or mask of the operator. For example, the display screen 120 may be integrated onto the mask of the operator such that the display screen 120 is a head-up display (HUD) that allows the operator to view the display screen 120 without moving his or her head and/or moving an arm that holds the camera 104, as shown in FIG. 9.

Figure 2:
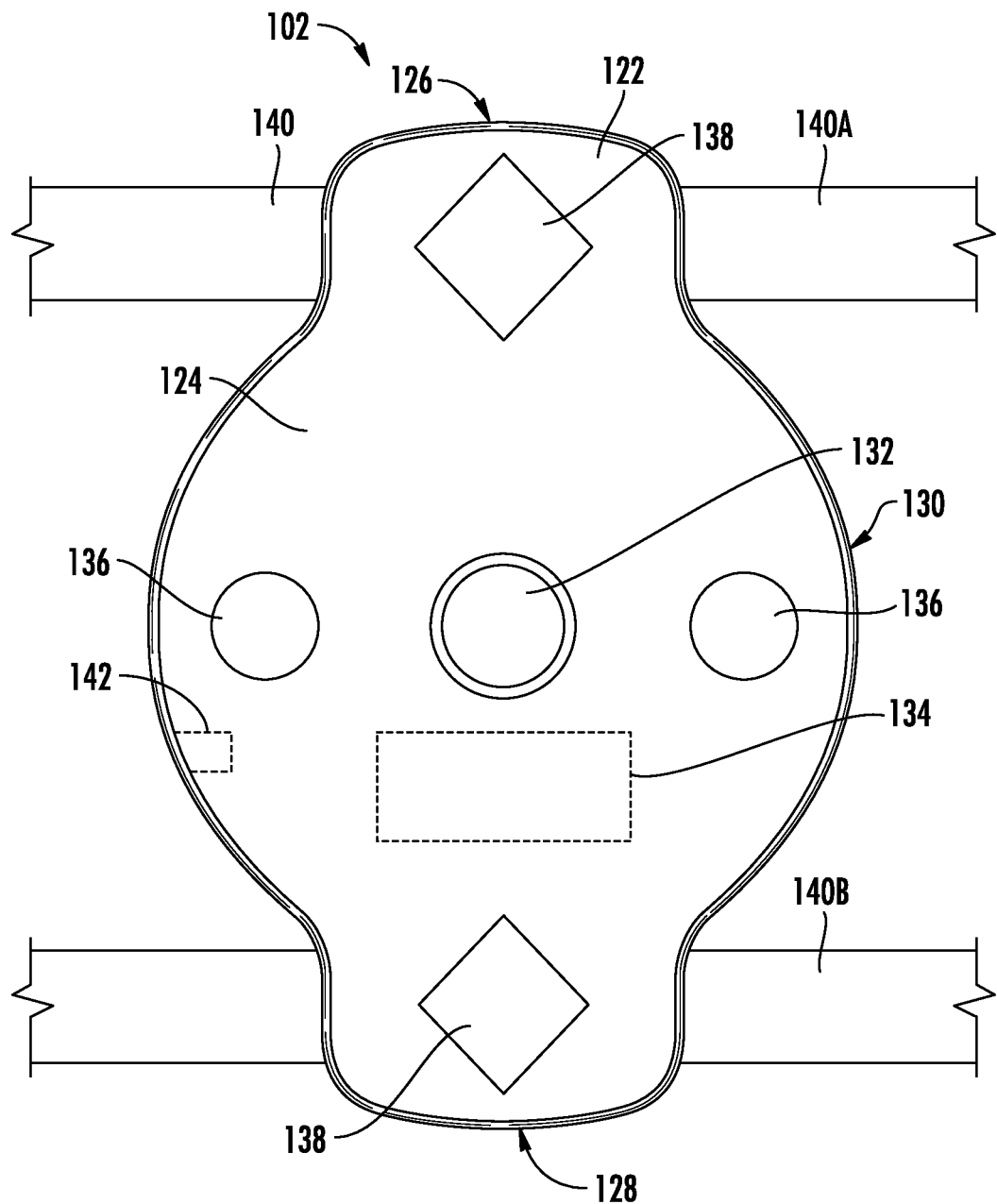
FIG. 2 illustrates a front view of a portable signaling device of the thermal imaging system according to an embodiment.

FIG. 2 illustrates a front view of the portable signaling device 102 according to an embodiment. The signaling device 102 includes a housing 122. Although only a front face 124 of the housing 122 is shown in FIG. 2, the housing 122 further includes a rear face 125 (shown in FIG. 4) that abuts against the wearer's clothing and/or equipment (such as against the air supply tank 112 shown in FIG. 1), and at least one sidewall 127 (shown in FIG. 4) that extends between the front face 124 and the rear face 125. The IR signals are emitted at least from the front face 124. The front face 124 may be curved or planar. The housing 122 in the illustrated embodiment has a vertically elongated shape that extends from a top end 126 to a bottom end 128, and a laterally-extending bulbous region 130 located medially between the top and bottom ends 126, 128. However, the shape of the housing 122 shown in FIG. 2 is exemplary only, and in other embodiments, the housing 122 may have a rectangular shape, a square shape, a pentagonal shape, a cylindrical shape, or the like.

The signaling device 102 further includes an IR emitter 132 held by the housing 122 and a control circuit 134 electrically connected to the IR emitter 132 within the housing 122. The IR emitter 132 is configured to emit pulses of mechanically-generated IR radiation as IR signals. The pulses of IR radiation have wavelengths in the infrared range, such as between 700 nm and 1 millimeter (mm) (or 1,000,000 nm). In an embodiment, the IR emitter 132 emits long wavelength IR pulses, which have wavelengths between 8 and 15 micrometers (μm) (or between 8,000 and 15,000 nm). The IR emitter 132 is located on or proximate to the front face 124, such that the IR signals are conveyed outward from the front face 124. Although the IR emitter 132 is shown in an approximate central location on the housing 122 in FIG. 2, the IR emitter 132 may have other relative locations on the housing 122 in other embodiments. Although only one IR emitter 132 is shown in FIG. 2, the signaling device 102 in other embodiments may include more than one IR emitter 132. For example, an additional IR emitter 132 may be located on the sidewall 127 (shown in FIG. 4) along the top end 126 and/or the bottom end 128. Optionally, all of the IR emitters 132 on the same signaling device 102 are controlled by the same control circuit 134 to emit the same IR pulses. Providing additional IR emitters 132 increases the range of angles that the IR pulses emitted by the signaling device 102 may be detected by the thermal imaging camera 104 (shown in FIG. 1). For example, when the signaling device 102 is worn on the back of a wearer with the top end 126 facing the wearer's head, if the wearer is crouched over in a crawling position, a thermal imaging camera 104 held by an operator behind the wearer may not receive IR pulses emitted from the emitter 132 on the front face 124, which may be directed vertically upward. But, the thermal imaging camera 104 would be able to detect IR pulses emitted by another IR emitter 132 located on the sidewall 127 along the bottom end 128, which would be directed towards the operator due to the orientation of the wearer.

In a preferred embodiment multiple signaling devices 102 are placed on different parts of a firefighter's outfit, including for example without limitation, on the SCBA pak, the firefighter's helmet, the firefighter's knee (front and back), elbows, shoulders, thighs, calves, hands and/or the firefighter's boots. Each signaling device 102 may have at least one unique pulse sequence detectable by the thermal imaging camera 104 (shown in FIG. 1). Once the IR radiation is detected, the unique pulse sequences are processed to identify the signaling devices 102 and relate individual signaling devices 102 to respective locations of the devices 102 on the wearer. The pulse sequences are further processed, individually and/or collectively with other detected signals, to provide detailed operational information regarding the firefighter wearing the signaling devices 102. Processing the pulse sequences received from individual signaling devices 102 provides operating parameters of the wearer and/or equipment of the wearer (e.g., air tank pressure, PASS alarm, etc). Processing the pulse sequences from multiple signaling devices 102 collectively, referred to as "collective interrogation," allows for more complex signal communication data to be transmitted and received, such as data to support a determination of risk profiles for the firefighter, and using distance and angle correlations for the signals received from the individual firefighter, and current data transmitted on the firefighter's status, calculations of the firefighter's position and/or orientation is determined which provides a risk determination for the firefighter. The position and/or orientation is then used in a virtual representation displayed to team members and/or others, such as on-scene commanders, support personnel, etc. Additionally, using distance and angle correlations for the signals received from multiple firefighters present on-scene, and current data transmitted on the firefighter's status, calculations of the firefighter's position and/or orientation is determined for each firefighter relative to other member of the team and that individual firefighter's mission within the team, which is then used in a virtual representation displayed to team members and/or others, such as on-scene commanders, support personnel, etc., as well as providing a risk profile for the entire firefighting team.

Optionally, the signaling device 102 may also include at least one visible light emitter 136. Two visible light emitters 136 are shown in FIG. 2, and are both located along the bulbous region 130 of the housing 122. It is recognized that the signaling device 102 may include more than two visible light emitters 136 in other embodiments. The visible light emitters 136 are configured to emit visible light in the wavelength range between approximately 380 nm to approximately 750 nm. The visible light emitters 136 may enhance the ability for the wearer wearing the signaling device 102 to be seen in a low visibility environment by other persons, such as other first responders, in the immediate vicinity. The at least one visible light emitter 136 may be controlled operate concurrently with the IR emitter 132. As used herein, concurrently means that two events overlap in time, although the events need not start or end at the same time. For example, in an emergency situation in which the wearer requires assistance, the IR emitter 132 may emit pulse sequences of IR radiation in a status message that requests immediate assistance and the at least one visible light emitter 136 may flash brightly and/or with a high frequency. Thus, an operator with the thermal imaging camera 104 may utilize both the received IR radiation in the status message and the visible light emitted by the emitter 136 to locate the wearer. Although the two visible light emitters 136 are shown as having a generally circular shape in FIG. 2, the visible light emitters 136 may have other shapes and/or orientations in other embodiments, such as triangular or arrow shapes.

The signaling device 102 may optionally include at least one reflector 138 on the housing 122. Two reflectors 138 are shown in FIG. 2. Each reflector 138 is configured to reflect visible light that impinges upon the reflector 138. At least some of the light may be reflected in a direction generally towards the source of the light, which enhances the ability for the wearer wearing the signaling device 102 to be seen in a low visibility environment by a person holding a flashlight, for example.

The signaling device 102 includes a fastener for removably attaching the signaling device 102 to the wearer's equipment or clothing. In an embodiment, the housing 122 is coupled to at least one strap 140. The housing 122 is coupled to two straps 140 in FIG. 2, with one strap 140A located proximate to the top end 126 of the housing 122 and a second strap 140B located proximate to the bottom end 128. The straps 140 may be used to fasten the signaling device 102 to an air supply tank 112, as shown in FIG. 1, by wrapping around the perimeter of the air supply tank 112.

The straps 140 may alternatively be wrapped around the leg of the wearer, the waist, the helmet, the arm, the harness assembly of the SCBA 110 (shown in FIG. 1), or the like. Optionally, the signaling device 102 may include at least one fastener in addition to, or as an alternative to, the straps 140. For example, the rear face 125 (shown in FIG. 4) of the housing 122 may include hook and loop patches, magnets, an adhesive patch, projections or pointed spikes, and the like, in order to attach the signaling device 102 to the wearer's clothing or equipment.

The signaling device 102 may further include a port 142 that is configured to provide an electrical connection between the signaling device 102 and the monitoring system 108 (shown in FIG. 1). For example, the port 142 may be an electrical connector that is configured to mate to an electrical connector at an end of the cable 118 shown in FIG. 1, to provide an electrical signal path between the control circuit 134 of the signaling device 102 and the monitoring system 108. The signaling device 102 may receive an input from the monitoring system 108 via the port 142. In an alternative embodiment, the signaling device 102 may include a radio frequency (RF) receiver instead of, or in addition to, the port 142, such that the signaling device 102 receives the input from the monitoring system 108 wirelessly through the RF receiver.

Figure 3:
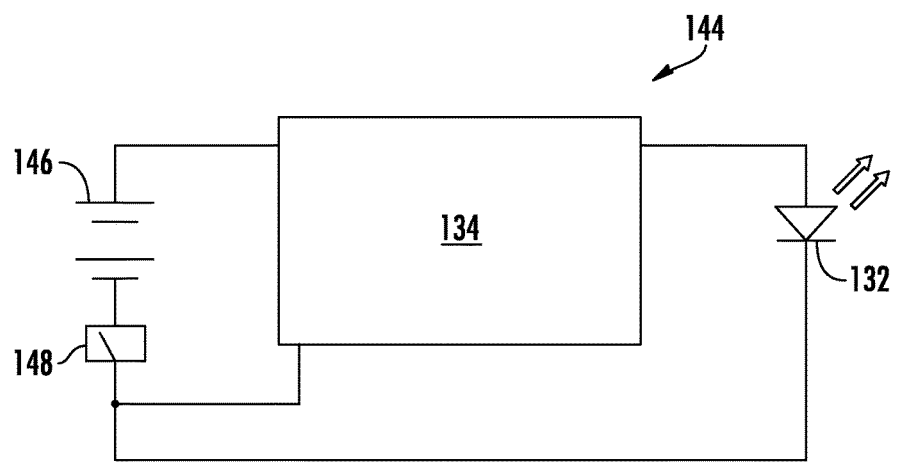
FIG. 3 is a simplified schematic illustration of an IR pulse transmitting circuit that may be used with the portable signaling device.

FIG. 3 is a simplified schematic illustration of an IR pulse transmitting circuit 144 that may be used with the signaling device 102 shown in FIGS. 1 and 2. The circuit 144 includes a power source 146, the control circuit 134, the IR emitter 132, and a switch 148. The power source 146 may be a disposable direct current (DC) battery that has a limited useful lifespan. For example, the disposable battery may supply sufficient current and voltage to operate the signaling device 102 for a period of time, such as from approximately eight hours to approximately sixteen hours. The disposable battery may be held in cavity of the housing 122 (shown in FIG. 2) that allows the disposable battery to be removed and replaced with another disposable battery to replenish the power supply. In another embodiment, the power source 146 may be embodiment as a rechargeable DC battery that has the ability to be recharged after each use or as needed.

The IR emitter 132 may be embodied as a semiconductor device that is configured to emit IR pulses. For example, the IR emitter 132 may be embodied as an IR light emitting diode (LED). In another embodiment, the IR emitter 132 may be embodied as a thermal emitter. For example, the IR emitter 132 may be a high-resistance conductor that generates heat-induced IR pulses. The IR emitter 132 may be a nickel-chromium wire conductor that generates an IR pulse based on the amount of radiant energy generated by the conductor in response to current transmitted through the conductor. In the exemplary embodiment, the IR emitter 132 is configured to emit a IR pulses within the long wavelength infrared spectrum, such that the signals having a wavelength from approximately 8 μm to approximately 15 μm.

The control circuit 134 controls the operation of the IR emitter 132. More specifically, the control circuit 134 is configured to activate and deactivate the IR emitter 132 and is configured to control the power supplied to the IR emitter 132 from the power source 146. For example, the control circuit 134 may be configured to control the electrical characteristics of the IR pulses, such as the frequency, wavelength, voltage, amplitude, intensity, or the like of the electromagnetic waves of IR radiation emitted by the IR emitter 132 for each pulse. IR frequencies may include, as determined by those skilled in the art, near-infrared, short-wavelength infrared, mid-wavelength infrared, long-wavelength infrared, far-infrared, and the like as useful in communicating within various environments where IR signal transmissions are found useful. Use of a signal specified wavelength, or combinations of wavelengths can be utilized to best communicate information within the team. In one preferred embodiment long-wavelength infrared is used. In another preferred embodiment combinations of different IR wavelengths are used to convey complex data transmissions and/or provide redundancy of messaging to ensure accuracy in processing of the transmission. The control circuit 134 may also be configured to control the timing of the IR pulses in the pulse sequences. The timing refers to the respective durations of each of multiple IR pulses in a single pulse sequence, and may also refer to the respective durations of pauses between successive or consecutive pulses in a sequence. For example, multiple IR pulses in the same pulse sequence may have the same or similar electrical characteristics, such as frequency and wavelength, but may have different durations from one another in order to provide different information to the thermal imaging camera 104. Thus, the control circuit 134 may differentiate the IR pulses based on the electrical characteristics of the pulses, the timing of the pulses, or both. By controlling the electrical characteristics of the IR pulses and the timing between IR pulses in a pulse sequence, the control circuit 134 is able to communicate data and other information in status messages using the IR pulse sequences generated by the IR emitter 132 as the mode of conveyance. The control circuit 134 optionally may include a microprocessor or the like.

The switch 148 is configured to enable (and disable) power to be transmitted from the power source 146 to the IR emitter 132 and to the control circuit 134. More specifically, the switch 148 is configured to activate and/or deactivate the signaling device 102, such as to turn the signaling device 102 on or off. The switch 148 may be a contact mechanism that includes at least one conductive contact that is configured to move to close and open the circuit 144 in order to turn on and turn off, respectively, the signaling device 102.

Figure 4:
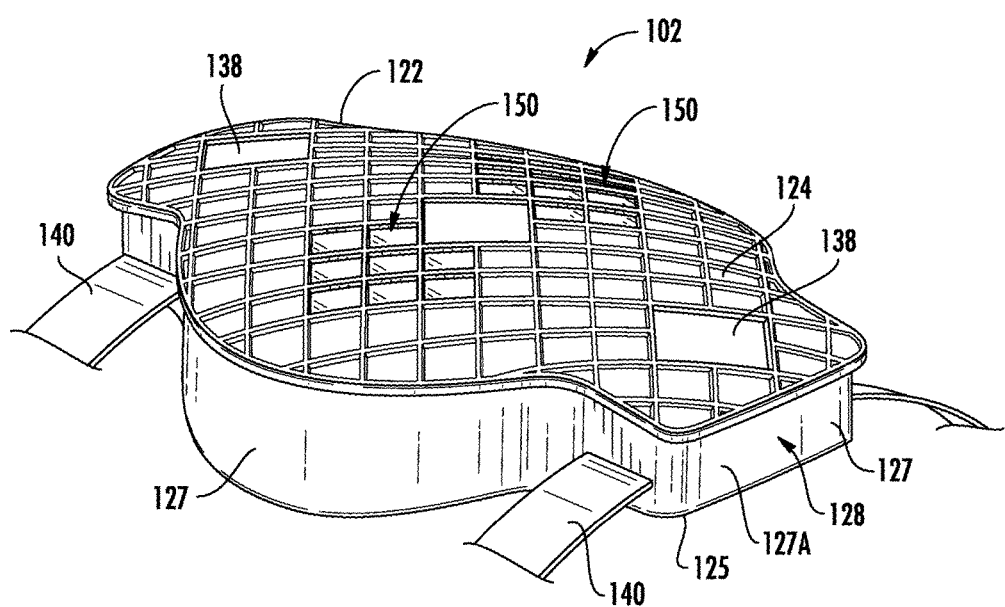
FIG. 4 is a perspective view of the portable signaling device formed in accordance with one embodiment.

FIG. 4 is a perspective view of the signaling device 102 formed in accordance with one embodiment. The housing 122 includes the front face 124, the rear face 125, and multiple sidewalls 127 that extend between the front face 124 and the rear face 125. The housing 122 may be fabricated from a plastic material, and optionally may include a fire or heat resistant material to enable the signaling device 102 to be utilized within a hazardous thermal environment. Two straps 140 extend through the housing 122 for fastening the signaling device 102 to the wearer or the wearer's equipment. The signaling device 102 includes two reflectors 138 disposed along the front face 124. In the illustrated embodiment, the front face 124 of the housing 122 defines two signal openings 150. Each IR emitter 132 (shown in FIG. 2) may be disposed within the housing 122 (between the front and rear faces 124, 125), such that the signal openings 150 allow the IR pulses generated by the IR emitter(s) 132 to be emitted from the housing 122.

The IR emitter 132 of the signaling device 102 shown in FIG. 4 may be a thermal emitter. For example, the IR emitter 132 may include a rotary disc that spins within the housing 122. The rotary disc includes at least one heat source, such as a high-resistance conductor. As the rotary disc spins, the heat source moves relative to the signal openings 150. When the heat source aligns with one of the signal openings 150, IR radiation is emitted through that signal opening 150. Thus, the characteristics of the IR pulses emitted from the signaling device 102 may be controlled by altering the energy supplied to the heat source and/or by modifying the speed that the rotary disc spins. It is recognized that the IR emitter 132 described with the embodiment of the signaling device 102 shown in FIG. 4 is merely one example embodiment. The signaling device 102 in other embodiments may have LEDs or other types of thermal emitters, such as thermal emitters that are not located on spinning discs (for example, thermal emitters on rotary shafts or are stationary).

Although not shown in FIG. 4, the signaling device 102 may include an IR emitter disposed along the sidewall 127A at the bottom end 128 of the housing 122. The IR emitter at the bottom end 128 may be useful for emitting IR pulses in a different direction than the IR emitter 132 (shown in FIG. 2) that emits IR pulses from the front face 124. For example, the IR emitter at the bottom end 128 may be useful for emitting IR pulses rearward of the wearer when the wearer is in a crouching, crawling, or laying position.

Figure 5:
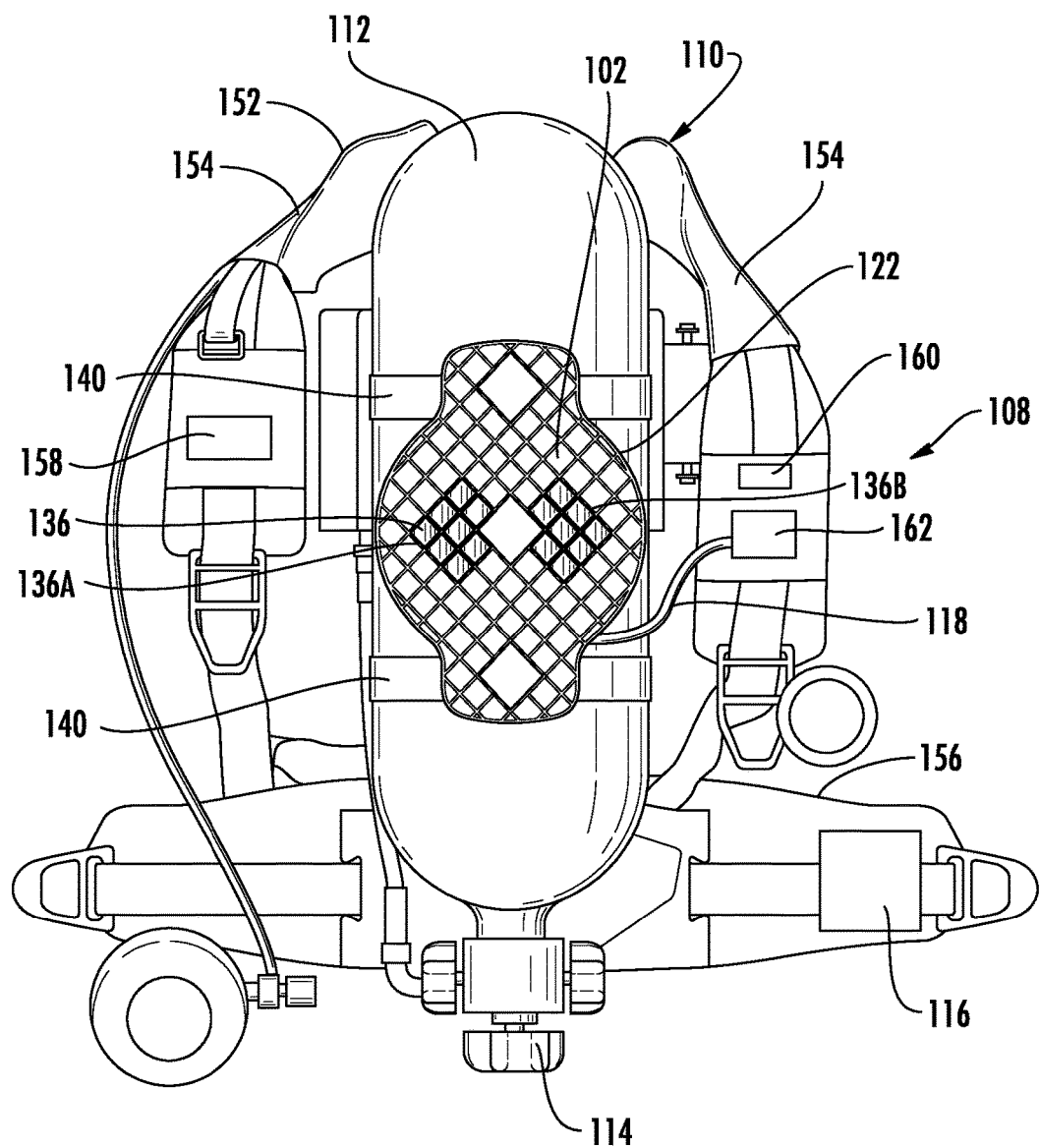
FIG. 5 is a rear view of the portable signaling device fastened to an air supply tank of a self-contained breathing apparatus (SCBA) according to an embodiment.

FIG. 5 is a rear view of the signaling device 102 fastened to an air supply tank 112 of an SCBA 110 according to an embodiment. For example, the straps 140 of the signaling device 102 extend around the perimeter of the air supply tank 112, which hold the rear face 125 (shown in FIG. 4) of the housing 122 in abutment with the surface of the air supply tank 112. In addition to the air supply tank 112, the SCBA 110 includes a harness assembly 152 to which the air supply tank 112 is mounted. The harness assembly 152 includes shoulder straps 154 and a waist strap 156 which allows the wearer to carry the harness assembly 152 and the air supply tank 112 mounted thereto.

In an embodiment, the harness assembly 152 is used to carry various equipment and sensors. For example, the harness assembly 152 is used to carry the monitoring system 108 that is configured to monitor operations of the wearer. The monitoring system 108 may include, for example, the pressure sensor 114 that measures an air pressure in the air supply tank 112, the motion sensor 116, a temperature sensor 158, a manually-operated user input device 160, and a controller 162. The temperature sensor 158 may be a thermistor or the like. The temperature sensor 158 may be configured to monitor an ambient temperature in the immediate vicinity of the wearer. Additional temperature sensors 158 may be installed on the harness assembly 152 to measure temperatures of at least some of the equipment. As described above, the motion sensor 116 may be an accelerometer, a magnetic sensor, a gyroscope, or the like. The motion sensor 116 is used to determine whether the wearer is moving or not at any given time, and may also be used to determine the speed and/or direction of movement of the wearer. The user input device 160 allows the wearer to manually select information to be conveyed via the signaling device 102. For example, the user input device 160 may have a pre-selected limited number of inputs, such as an emergency, help-requested input. The user input device 160 may have one or more buttons, toggles, or the like to allow the wearer to manually manipulate the user input device 160 to select a desired input. In an embodiment, the user input device 160 may have voice command functionality. For example, the device 106 may include or be operably connected to a microphone that receives an audible voice command input from the wearer, such as "evacuate," "firefighter down," or "request help." The locations of the components, such as the temperature sensor 158, the motion sensor 116, the pressure sensor 114, and the user input device 160, in the illustrated embodiment shown in FIG. 5 are merely for example, and at least some of these components may have other locations along the harness assembly 152 in other embodiments.

In an embodiment, the controller 162 is configured to communicate directly with each of the other components of the monitoring system 108, such that the individual components convey data and other information to the controller 162. The controller 162 may be conductively connected to each or at least some of the other components of the monitoring system 108 via electrical wires and/or cables (not shown). Alternatively, the controller 162 may communicate wirelessly with at least some of the other components. For example, the controller 162 may have an RF receiver that receives wireless signals from the temperature sensor 158, the motion sensor 116, the pressure sensor 114, and/or the actuator 160. The controller 162 receives data parameters from the sensors 158, 116, and 114. For example, the controller 162 may receive the temperature of the ambient environment of the wearer and/or the temperature of equipment worn by the wearer from the temperature sensor 158. The controller 162 also receives the pressure of the air supply tank 112 from the pressure sensor 114 and the current movement status of the wearer from the motion sensor 116. The controller 162 also receives any inputs manually entered by the wearer via the user input device 160.

The controller 162 is configured to process the information received from the other components and to generate an output that is conveyed to the signaling device 102 via a cable 118 for the signaling device 102 to convey the information in the output as a status message formed by one or more IR pulse sequences. In an alternative embodiment, the sensors and other components of the monitoring system 108 may communicate with the control circuit 134 (shown in FIG. 3) of the signaling device 102 that is housed within the housing 122, and the control circuit 134 processes the information received from the components to generate the status message emitted by the IR emitter 132 (shown in FIG. 3). The controller 162 and/or the control circuit 134 may include one or more processors or another processing device that is configured to analyze and process the information received. As used herein, the term "processor" may include any computer or processor-based system, including systems that use microcontrollers, microprocessors, reduced instruction set computers (RISC), application specific integrated circuits (ASICs), field programmable gate arrays (FPGAs), logic circuits, and any other circuit or processor capable of executing the functions described herein. The above examples are exemplary only, and are thus not intended to limit in any way the definition and/or meaning of the term "microprocessor".

The controller 162 is configured to process the received information to generate an output that is conveyed to the signaling device 102. The controller 162 may process the information by selecting which information to convey in the output to the signaling device 102 and how to convey that information. For example, the controller 162 may receive a data parameter from the pressure sensor 114 that represents the current air pressure in the air supply tank 112 as an integer value, such as 20,000 kPa. The controller 162 may determine whether to present the data parameter as the integer value in the output to the signaling device 102 or, for example, to convert the data parameter to a level, range, or percentage value, such as 30% air supply remaining. The same is true for the temperature sensor 158, such that the output generated by the controller 162 may indicate the measured temperature of the ambient environment of the wearer, and/or whether the temperature is at a non-hazardous or hazardous level. Similarly, the controller 162 may interpret received data from the motion sensor 116 to generate an output that indicates simply whether the wearer is stationary or moving, and the direction of movement of the wearer if the wearer is moving. The output may be conveyed to the signaling device 102 conductively via the cable 118. Alternatively, the controller 162 may include an RF transmitter (for example, a transceiver that includes both a receiver and a transmitter) that is configured to transmit the output to the signaling device 102 wirelessly. The signaling device 102 in such alternative embodiment includes an RF receiver to receive the output from the controller 162. The output from the controller 162 is received as an input by the signaling device 102. As described above, in an alternative embodiment the control circuit 134 of the signaling device 102 may be configured to process the received information to select the information and the format of the information to transmit to the thermal imaging camera 104 (shown in FIG. 1) instead of, or in addition to, the controller 162.

Figure 6:
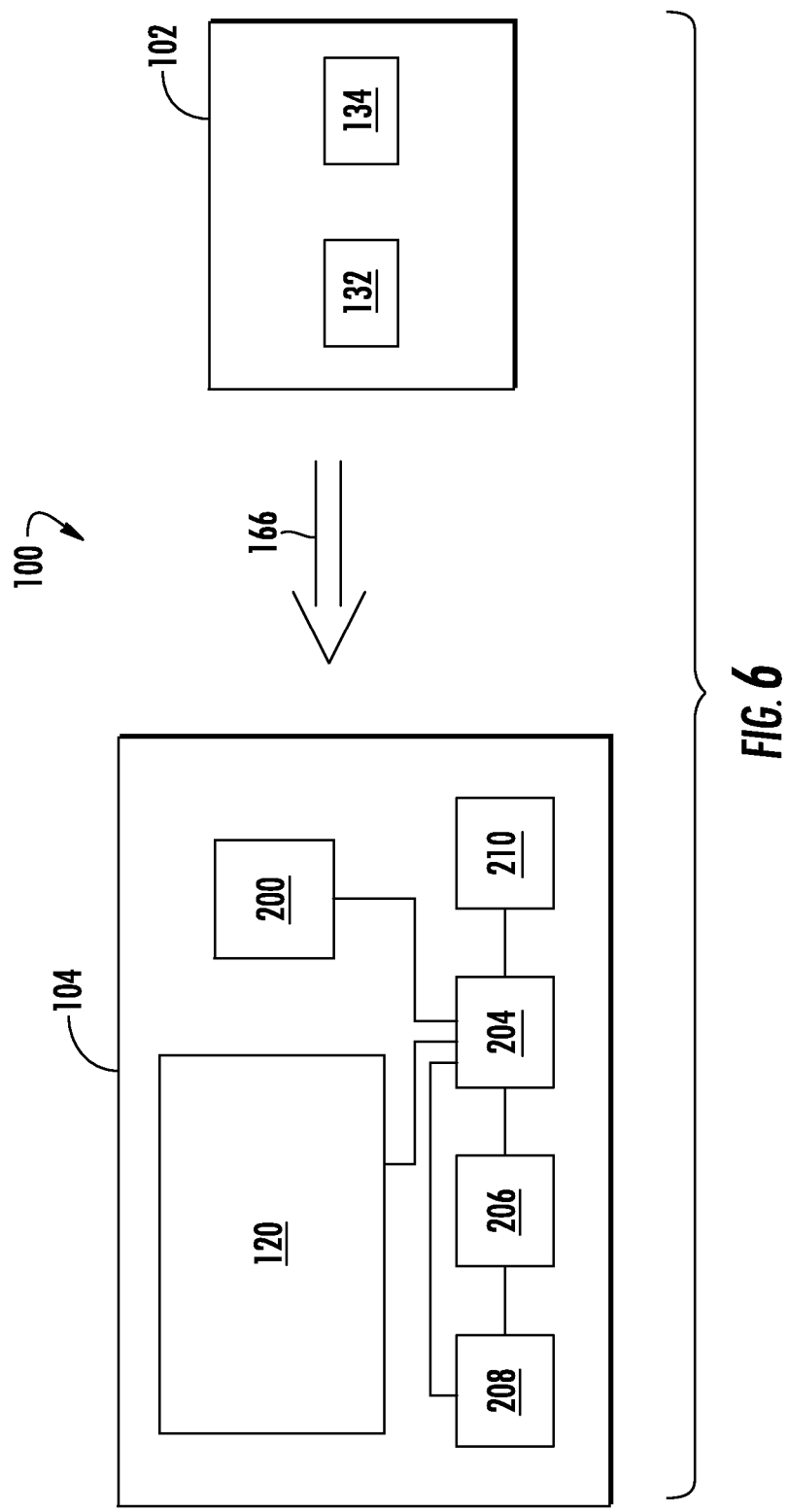
FIG. 6 is a simplified illustration of a thermal imaging system formed in accordance with one or more embodiments.

FIG. 6 is a schematic diagram of the thermal imaging system 100 including the portable signaling device 102 and the thermal imaging camera 104. The signaling device 102 includes the IR emitter 132 and the control circuit 134, which controls the IR pulses generated by the IR emitter 132 to form the status message 166. The control circuit 134 may be implemented in hardware on a printed circuit board, for example, using inductors, resistors, capacitors, etc. Optionally, the control circuit 134 may be implemented as one or more processors. The control circuit 134 may include a set of instructions (for example, software) installed thereon. The control circuit 134 may use the set of instructions to analyze the input received from the monitoring system 108 (shown in FIG. 5). In response to the received input, the control circuit 134 is configured to operate the IR emitter 132 to generate one or more IR pulse sequences based on the instructions. For example, the control circuit 134 may use the set of instructions to convert a data parameter representative of the pressure of the air supply tank 112 (shown in FIG. 5) into corresponding properties of an IR pulse sequence (such as wavelength of the IR pulses, the timing between the IR pulses in the IR pulse sequence, the intensity of the IR pulses, or the like) to be generated and emitted by the IR emitter 132. The signaling device 102 may be configured to transmit the status message 166 automatically upon receipt of an input from the monitoring system 108 or periodically at a set time interval. The signaling device 102 also may transmit the message 166 continuously or repetitiously, such as if an emergency alarm state is detected. Thus, in one or more embodiments, manual actuation by a wearer is not required for the signaling device 102 to generate and convey the message 166.

The thermal imaging camera 104 is configured to detect the IR pulse sequences to receive the status message 166. The thermal imaging camera 104 is further configured to interpret the properties of the received IR pulse sequences to determine the information conveyed, such as a data parameter for the pressure of the air supply tank 112 that indicates a remaining quantity of air in the air supply tank 112. As described in more detail herein, the thermal imaging camera 104 is also configured to generate a display message based on the received IR pulse sequences and to display the display message on the display screen 120 of the thermal imaging camera 104. The display message includes visual indicia representative of the operating status of the wearer. Therefore, the signaling device 102 is configured to relay one or more specific pieces of information to the thermal imaging camera 104 in the status message 166 that is conveyed by one or more IR pulse sequences.

The status message 166 is used to convey an operating status of the wearer on which the signaling device 102 is mounted. For example, the input received by the signaling device 102 from the monitoring system 108 (shown in FIG. 5) represents an operating status associated with the wearer. The operating status may include (for example, provide information about) a health condition of the wearer, a condition of the equipment worn by the wearer, a movement status of the wearer relative to the ambient environment, a location of the wearer, an orientation of the wearer, and/or an identification of the wearer. The control circuit 134 of the signaling device 102 is configured to operate the IR emitter 132 to generate and transmit the message 166 based on the input. The message 166 therefore represents the operating status associated with the wearer. The message is formed and conveyed via one or more pulse sequences of IR radiation emitted by the IR emitter 132. Each IR pulse sequence may represent data or other information regarding the operating status associated with the wearer. For example, at least a first pulse sequence in the message 166 may represent a health condition of the wearer, at least a second pulse sequence in the message 166 may represent an equipment condition of equipment worn by the wearer, at least a third pulse sequence in the message 166 may represent wearer movement of the wearer, and at least a fourth pulse sequence in the message 166 may represent a wearer identifier that identifies the wearer.

Figure 7:
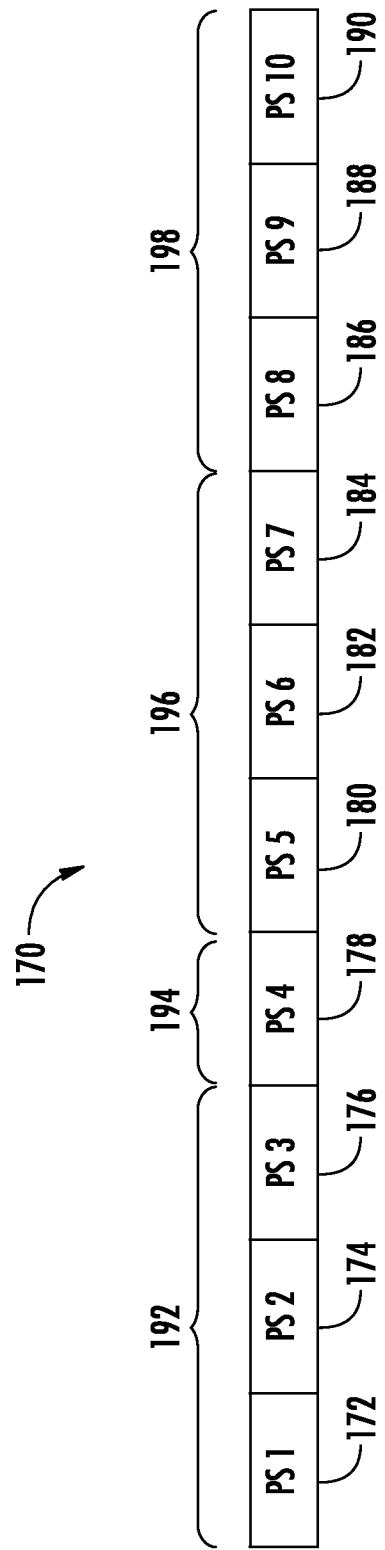
FIG. 7 illustrates a message that may be generated by the portable signaling device according to an embodiment.

FIG. 7 illustrates a status message 170 that may be generated by the signaling device 102 (shown in FIG. 6) according to an embodiment. The message 170 may be the status message 166 shown in FIG. 6. The message 170 includes a plurality of IR pulse sequences 172-190, labeled PS1 through PS10 in FIG. 7. Each IR pulse sequence is comprised of at least one, and typically a series of, individual IR pulses generated and emitted by the IR emitter 132 (shown in FIG. 6). The IR pulse sequences 172-190 each provide different information, such as different data parameters. The IR pulse sequences 172-190 are unique from one another. For example, the IR pulse sequences 172-190 may be distinguishable from one another in the number of IR pulses in each sequence, in the electrical characteristics of the IR pulses (for example, the frequency, wavelength, voltage, amplitude, intensity, or the like), in the durations of each of the IP pulses, and/or the durations of the pauses between successive pulses in each sequence.

In the illustrated embodiment, the first IR pulse sequence 172 in the message 170 may represent the identity of the wearer. For example, the IR pulse sequence 172 may provide the first and/or last name, code name, identifying number, or other identification for the wearer that wears the signaling device 102 (shown in FIG. 6). The second pulse sequence 174 may represent the identity of the team or group to which the wearer is associated. The team or group may be an identification of a department, such as if the wearer is a firefighter or another first responder. Thus, if the wearer is lost or incapacitated, an operator using a thermal imaging camera 104 (shown in FIG. 6) that locates the wearer may be able to determine the name and affiliated group of the wearer. The third IR pulse sequence 176 may represent an identity of the signaling device 102. A wearer may carry multiple signaling devices 102. Identification of the signaling device 102 that is emitting IR pulses being received by the thermal imaging camera 104 may provide useful information to the operator, such as the direction that the wearer is facing. For example, if the wearer is facing the operator, the thermal imaging camera 104 held by the operator may receive the message 170 from a signaling device 102 located along the front of the wearer, and if the wearer is facing away from the operator, a signaling device 102 on the rear of the wearer may transmit the message 170 that is received at the thermal imaging camera 104. The three IR pulse sequences 172-176 may represent a wearer identifier series or string 192 that identifies the wearer. Optionally, the wearer identifier string 192 may include more or less than the three IR pulse sequences 172-176 described, and may include at least some different identification information, in other embodiments.

The fourth IR pulse sequence 178 may represent an alarm status of the wearer. For example, the alarm status may indicate whether the wearer is in a non-alarm state, a pre-alarm state, or an alarm state. If the wearer is in a non-alarm state, no action may be requested. The pre-alarm state indicates that the equipment of the wearer may be in a health condition that is relatively close to a critical level but is not currently at the critical level. For example, the wearer may be in a pre-alarm state if the motion sensor 116 (shown in FIG. 5) does not detect movement of the wearer for a period of time greater than a first time threshold; if a detected heart rate of the wearer is greater than a first heart rate threshold; and/or if the temperature sensor 158 detects that the temperature of the ambient environment is above a first temperature threshold. In a pre-alarm state, the equipment of the wearer, such as a personal alert safety system (PASS) device (not shown), may provide a notification to the wearer, such as by an audible alert. The message 170 may relay the state of the wearer to the operator holding the thermal imaging camera 104 (shown in FIG. 6). The alarm state, or full alarm state, is an emergency condition. The wearer may be in an alarm state if the motion sensor 116 does not detect movement of the wearer for a period of time greater than a second time threshold that is longer than the first time threshold; if a heart rate monitor (not shown) detects that the heart rate of the wearer is greater than a second heart rate threshold that is greater than the first heart rate threshold; and/or if the temperature sensor 158 detects that the temperature of the ambient environment is above a second temperature threshold that is higher than the first temperature threshold. The detection of the alarm status of the wearer may be significant as it may be difficult to determine the condition of the wearer and the equipment of the wearer visually, even when using thermal imaging to provide visual thermal images. The alarm status of the wearer represents the wearer condition 194. Optionally, additional information may be provided through one or more other IR pulse sequences to convey the wearer condition 194 of the wearer to an operator with a thermal imaging camera 104.

The fifth, sixth, and seventh IR pulse sequences 180-184 represent an equipment condition string 196 of the message 170. For example, the fifth IR pulse sequence 180 may provide a status of the manually-operated user input device 160 (shown in FIG. 5), such as whether the wearer has selected any of the inputs of the user input device 160 for transmission to the operator. The sixth IR pulse sequence 182 may provide a data parameter indicative of the air pressure in the air supply tank 112 (shown in FIG. 5) as monitored by the pressure sensor 114 (FIG. 5). The data parameter may indicate the remaining air pressure (e.g., the quantity of air remaining in the tank 112) as an integer value, as a percentage value based on the initial air pressure of the full tank 112, as a time value representative of time remaining before low air pressure (e.g., 20 minutes remaining), as a range value (e.g., between ¼ and ½ supply remaining, or the like). The sixth IP pulse sequence 184 may indicate whether the air supply tank 112 is in a pre-alarm state or an alarm state. For example, the air supply tank 112 is in the pre-alarm state responsive to the air pressure being lower than a first pressure threshold, and the air supply tank 112 is in the alarm state responsive to the air pressure being lower than a second pressure threshold that is below the first pressure threshold. The seventh IR pulse sequence 184 may provide a data parameter indicative of the temperature surrounding the wearer as measured by the temperature sensor 158 (FIG. 5). Like the pressure data parameter, the temperature may be presented in various ways, such as an integer value, a range value, or as a general word value (e.g., "non-hazardous temperature").

In the illustrated embodiment, the eighth, ninth, and tenth IR pulse sequences 186-190 represent a wearer movement string 198 of the message 170. The wearer movement string 198 is monitored by the motion sensor 116 (shown in FIG. 5). For example, the eighth IR pulse sequence 186 may provide a motion status, such as if the wearer is currently moving (for example, walking or crawling) or is currently stationary. The ninth pulse sequence 188 may provide the time elapsed since the last recorded movement of the wearer if the wearer is currently stationary. The tenth pulse sequence 190 may provide the direction of movement of the wearer.

It is recognized that the IR pulse sequences 172-190 shown and described in the illustrated message 170 in FIG. 7 are merely exemplary. Other messages conveyed by the signaling device 102 (shown in FIG. 6) may include more or less than ten IR pulse sequences, and/or the pulse sequences in other messages may provide different information than information provided by the IR pulse sequences 172-190. For example, another pulse sequence that is not shown in FIG. 7 may provide a location of the wearer. The location of the wearer may be presented in terms of a region or area of the building in which the wearer and/or operator is located, in terms of global positioning coordinates, and/or in terms of a relative position from the thermal imaging camera (e.g., 50 feet ahead in northwest direction). Another pulse sequence could represent the orientation of the wearer. For example, it may be determined whether the wearer is standing, crouching, crawling, or lying down based on the information received from one or more signaling devices 102 on the wearer. The orientation may be determined at least in part on the height of each transmitting signaling device 102 relative to the ground or floor. The thermal imaging camera 104 may also be able to determine the orientation of the wearer based on which signaling devices 102 are transmitting status messages that are received by the thermal imaging camera 104. For example, if the thermal imaging camera 104 receives status messages from both a first signaling device 102 disposed on the heel of the wearer's boot and a second signaling device 102 disposed on the tank 112, then the thermal imaging camera 104 may determine that the wearer is facing away from the camera 104. Based on the height of the second signaling device 102 from the ground or relative to the first signaling device 102, the camera 104 can determine whether the wearer is standing or kneeling.

The message 170 in FIG. 7 illustrates that the signaling device 102 conveys data and other information to the thermal imaging camera 104 (shown in FIG. 6) via sequences of IR pulses, such that the thermal imaging camera 104 may receive more complex information than the typical IR radiation used to form images of the surrounding on the display screen 120 (FIG. 6).

Referring now back to FIG. 6, the thermal imaging system 104 includes an IR detector 200, a controller 204 that includes one or more processors, and the display screen 120. The thermal imaging camera 104 may also include a memory or storage device 206 for storing various instructions for operating the thermal imaging camera 104 and/or storing images generated by the thermal imaging camera 104, messages received, recording logs, and/or other data. The IR detector 200 is configured to receive the status message 166 from the portable signaling device 102. More specifically, the IR detector 200 detects the one or more pulse sequences of IR radiation that form the status message 166. The IR detector 200 may be configured to receive pulse sequences from multiple different signaling devices 102 on the same wearer and/or on different wearers. The IR detector 200 is also configured to detect ambient IR radiation in the surrounding environment.

The processor 204 is configured to analyze the one or more pulse sequences detected by the IR detector 200. The processor 204 is further configured to generate a display message for presentation of the display message on the display screen 120. The display message is based on the one or more pulse sequences of the received status message 166. The display message includes visual indicia representative of the operating status of the wearer. The processor 204 may generate the display message using a set of instructions, a look-up table, or the like, stored in the memory 206 in order to generate the visual indicia in the display message based on the specific IR pulse sequences received in the status message 166.

In an embodiment, the display message also includes a graphical thermal image representative of the surrounding environment that is based on the detected ambient IR radiation. For example, the processor 204 uses the ambient IR radiation to generate thermal graphical images displayed on the display screen 120. The thermal imaging camera 104 may be configured to display the visual indicia representative of the operating status of the wearer concurrently with the graphical thermal images of the surrounding environment. The visual indicia includes at least one of text (e.g., words, abbreviations, etc.), numbers, objects, or symbols. For example, the visual indicia may be overlaid over at portion of the thermal image on the display screen 120. In an embodiment, the visual indicia associated with a first wearer may be located at least proximate to a graphical representation of the wearer in the graphical image on the display screen to associate the visual indicia with the graphical representation of the wearer. The display message may include visual indicia associated with more than one wearer, such as if more than one wearer is viewable in the surrounding environment. The thermal imaging camera 104 may store the overlaid images in the memory 206 and/or transmit the images to a remote location. As described above, the thermal imaging camera 104 may be handheld or attached to a portion of the wearer's equipment such as, for example, a helmet or mask.

Although the display screen 120 is shown in FIG. 6 as being generally contained within a common enclosure or housing as the other components of the thermal imaging camera 104, in an alternative embodiment the display screen 120 may be part of a display device that is remote from the common enclosure and operably connected to the controller 204. For example, the display device may be conductively connected to the controller 204 via an electrical wire or cable, or may be wirelessly connected via a communication circuit.

In an embodiment, the thermal imaging camera 104 further includes a user input device 208 that is operably connected to the controller 204. The user input device 208 in one embodiment includes a microphone (not shown) that is configured to receive voice commands from the operator of the thermal imaging camera 104. The controller 204 may be configured to customize or manipulate the visual indicia of the display message that is shown on the display screen 120 based on a voice command received via the user input device 208. The visual indicia in the display message may be associated with one or more specific portions of the operating status identified in the voice command. For example, in response to receiving a command to "show Jones," the controller 204 may generate a display message that highlights or emphasizes a graphical representation of the wearer identified as "Jones" in the display screen 120 while greying out, dimming, or otherwise de-emphasizing the surrounding environment and the graphical representations of other wearers that are not Jones. The visual indicia may include providing a highlighted outline around the graphical representation of Jones in the display screen 120, flashing, changing the color, and/or increasing the brightness of the graphical representation of Jones. In addition to emphasizing the graphical representation of Jones in the display screen 120, the display message may also show visual indicia that provide the operational status of Jones, such as whether Jones is in an alarm state. In addition to, or as an alternative to, the microphone, the user input device 208 may include one or more buttons, toggles, switches, or the like that allow a user to manually enter one or more selected user commands.

In one embodiment, the IR emitter 132 of the signaling device 102 may transmit status messages continuously, repetitively, and/or periodically at a determined interval. The IR detector 200 may be a passive component that continuously monitors for IR pulse sequences from one or more signaling devices 102 and/or continuously detects the ambient IR radiation from the environment. In an alternative embodiment, the IR emitter 132 does not continuously transmit, such that the thermal imaging camera 104 is configured to establish a communication link between the camera 104 and the signaling device 102 prior to receiving status messages 166 from the signaling device 102. For example, the thermal imaging camera 104 may include a communication circuit 210 that is operably connected to the controller 204. The communication circuit 210 may represent hardware and/or software that is used to communicate with other devices and/or systems, such as one or more portable signaling devices 102 located on the same wearer or on different wearers. The communication circuit 210 may include a transceiver and associated circuitry (e.g., an antenna) for wireless bi-directional communication of various types of messages, such as linking messages, status messages, and/or the like. The communication circuit 210 may be configured to transmit messages to specific designated signaling devices 102 and/or to broadcast messages indiscriminately. The initialization message optionally may be encrypted or encoded. In an embodiment, the communication circuit 210 is configured to transmit an initialization message that requests one or more portable signaling devices 102 to initiate or commence the generation of the pulse sequences of IR radiation. Upon receiving the initialization message, the signaling device 102 may begin emitting pulse sequences of IR radiation to transmit the status message to the thermal imaging camera 104.

The thermal imaging system 100 described herein is configured to have a field of view that is greater than a line of sight of the operator and/or wearer. For example, the IR detector 200 of the thermal imaging camera 104 is configured to receive status messages emitted from the one or more signaling devices 102 within a range that is greater than a range that the operator holding the camera 104 is able to see using his or her eyes. Since the status messages are transmitted using IR pulses, such pulses may penetrate areas of low light, areas having smoke or other entrained particles in the air, and/or areas having furniture, walls, and/or other debris between the signaling device 102 and the camera 104. Thus, the thermal imaging camera 104 may be configured to receive status updates from wearers that are outside of the line of sight of the operator, such that the operator is able to track the wearers using the camera 104.

Figure 8:
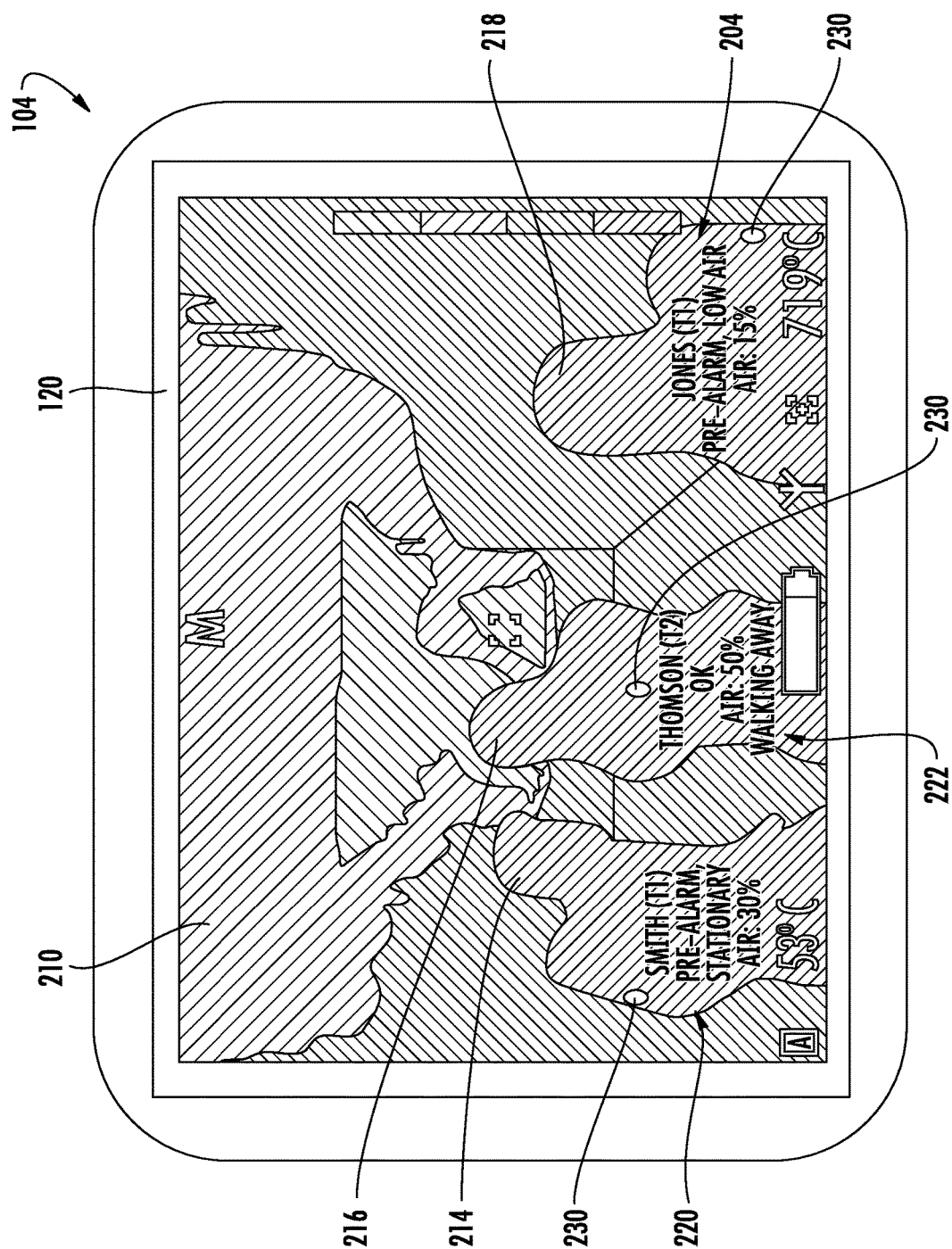
FIG. 8 illustrates a display screen of a thermal imaging camera of the thermal imaging system according to an embodiment.

FIG. 8 illustrates the display screen 120 of the thermal imaging camera 104 according to an embodiment. The display screen 120 displays a display message generated by the controller 204 of the thermal imaging camera 104. The display message includes a visual thermal image 210 (also referred to as graphical image 210) of the surrounding environment that is based on the ambient IR radiation detected by the IR detector 200 (shown in FIG. 6). Three wearers 214, 216, 218 are shown in the visual thermal image 210. The three wearers 214-218 are located in a low visibility environment, which is a smoke-filled corridor due to an uncontrolled fire. Although not shown, each wearer 214-218 carries at least one portable signaling device 102 (shown in FIG. 6). The display message further includes visual indicia that represents the operating status associated with the wearers 214, 216, 218. Thus, as shown in FIG. 8, the thermal imaging camera 104 is configured to generate a display message presented on the display screen 120 that includes some aspects (e.g., the graphical thermal image 210) based on the ambient IR radiation in the surrounding environment and other aspects (e.g., the visual indicia) based on the IR pulse sequences received from the portable signaling devices 102.

In an embodiment, the visual indicia is overlaid over the graphical image 210 of the surrounding environment. Optionally, the visual indicia may be overlaid over multiple thermal images that are displayed on the display screen 120 over time. The visual indicia include words, numbers, objects, and/or symbols that provide information about the operating status of the corresponding wearer. For example, the visual indicia may represent a wearer condition of the corresponding wearer, an equipment condition of equipment worn by the wearer, wearer movement of the wearer, wearer location, wearer orientation, and/or a wearer identifier of the wearer.

In an embodiment, the thermal imaging camera 104 is configured to display visual indicia for each of the multiple wearers 214-218 in the field of view of the thermal imaging camera 104. For example, a first set 220 of visual indicia corresponds to the left-most wearer 214, a second set 222 of visual indicia corresponds to the center wearer 216, and a third set 224 of visual indicia corresponds to the right-most wearer 218 in the thermal image 210. The processor 204 (shown in FIG. 6) may display the first set 220 of visual indicia proximate to a graphical representation of the left-most wearer 214 on the display screen 120, the second set 222 proximate to a graphical representation of the center wearer 216, and the third set 224 proximate to a graphical representation of the right-most wearer 218 to indicate the relationship between the visual indicia 220-224 and the corresponding wearer 214-218.

The thermal imaging camera 104 is configured to receive status messages from all three signaling devices on the three wearers 214-218, and is further configured to process the status messages to generate appropriate visual indicia associated with each of the wearers 214-218 in order to indicate to the operator the operating status of each wearer 214-218. For example, the message detected by the ID detector 200 (shown in FIG. 6) may be a first message from a first signaling device 102 (FIG. 6) worn by the left-most wearer 214, and the first set 220 of visual indicia displayed on the display screen 120 is first visual indicia that is based on the first message. The IR detector 200 may be further configured to receive a second message from a second portable signaling device 102 worn by the center wearer 216. The processor 204 (shown in FIG. 6) may be configured to concurrently display the first set 220 of visual indicia and the second set 222 of visual indicia (e.g., second visual indicia) that is based on the second message on the display screen 120. In the illustrated embodiment, the processor 204 further displays the third set 224 of visual indicia concurrently with the first and second sets 220, 222, such that an operating status of each of the three wearers 214-218 in the image 210 are displayed and observable to an operator using the thermal imaging camera 104. The visual indicia of each set 220-224 are displayed on the display screen proximate to the representation of the corresponding wearer 214-218 on the graphical thermal image 210, which allows the operator to associate the relevant visual indicia with each of the wearers 214-218.

In the illustrated embodiment, the sets 220-224 of visual indicia each provide a highlighted marker 230 which identifies the location of the signaling device 102 (shown in FIG. 6) that emitted the message used to generate the visual indicia. The first set 220 of visual indicia provides aspects of the operating status of the left-most wearer 214, although not necessarily all of the information that is provided in the message. For example, the first set 220 of visual indicia provides a wearer identifier as "Smith", who is associated with "T1" or Team 1. The first set 220 further indicates that Smith is in a "Pre-alarm" condition due to remaining "stationary," and the Smith has "30%" of air supply remaining in the air supply tank. The second set 222 includes similar information, such as that the center wearer 216 is identified as "Jones" from "T2" or Team 2. Jones is "OK", meaning that Jones is not in an alarm condition or a pre-alarm condition. Jones is currently "Walking away" from the operator with the thermal imaging camera 104, and Jones has "50%" of air remaining. The third set 224 of visual indicia associated with the right-most wearer 218 indicates that the wearer 218 is "Thomson" from Team 2. Thomson is in a pre-alarm state due to low air pressure, as the air pressure in the air supply tank is currently at only "15%". The visual indicia shown and described in FIG. 8 are merely exemplary. Different information representing the operating status of each of the wearers 214-218 may be displayed in other embodiments, and/or the information may be presented in a different manner, such as through different words, symbols, numbers, and objects than the visual indicia shown in FIG. 8.

In an embodiment, the controller 204 of the thermal imaging camera 104 is configured to generate updated display messages to present visual indicia representative of an update operating status of each of the wearers 214-218 as well as updated graphical images of the surrounding environment. The controller 204 may generate the updated display messages periodically at a regular interval or responsive to receiving an updated status message from one or more of the portable signaling devices 102. Optionally, the controller 204 may be configured to generate an updated display message responsive to the operating status of one of the wearers 214-218 indicating an alarm state. Furthermore, the controller 204 may generate an updated display message responsive to receiving a request or user command from the operator of the thermal imaging camera 104 to display an updated operating status of one or more of the wearers 214-218. The operator may submit the user command using the user input device 208 (shown in FIG. 6).

Each status message received by the thermal imaging camera 104 may include a set of information related to the operating status of the corresponding wearer. For example, each status message may include the all or at least some of the information described in the status message 170 shown in FIG. 7, such as the identity of the wearer, various data parameters related to the condition of the wearer (e.g., heart rate, temperature surrounding the wearer, etc.), a motion status of the wearer, a location of the wearer, an orientation of the wearer, various data parameters related to the equipment worn by the wearer, and the like. In an embodiment, the controller 204 of the thermal imaging camera 104 is configured to selectively display information received in the status messages to the operator on the display screen 120. For example, the thermal imaging camera 104 may discriminate among the information received to determine which subsets of information to include in the display message and which subsets of information to withhold from presenting on the display screen to avoid oversaturating the operator with information. Thus, the thermal imaging camera 104 in an embodiment generates the visual indicia to represent a subset, but not the entire set, of the information corresponding to the operating status of the wearer.

In an embodiment, the controller 104 may select the information to display as visual indicia on the display message by prioritizing the information received according to a set of rule-based instructions. The rule-based instructions may be default instructions stored in the memory 206 and/or user-customized instructions selected by the operator. For example, one default rule may be to assign information indicating an alarm status as high priority information that is always presented on the display screen 120. Thus, if a status message indicates that the air pressure or quantity of remaining air in an air supply tank is in an alarm state, then the controller 104 characterize this information as high priority and displays the information to the operator on the display screen 120. Other status information that may be marked as high priority is information that one of the wearers is incapacitated (e.g., man down), information that one of the wearers has been ordered to evacuate, or the like. On the other hand, if the air pressure in the tank is not within an alarm state or a pre-alarm state, the controller 104 may characterize this information as lower priority and may not display the lower priority information on the display screen 120. In an embodiment, the operator may submit user commands that affect which information is shown as visual indicia on the display screen 120. For example, even if the air pressure in a tank of one wearer is not in an alarm or pre-alarm state, the operator may submit a user command to show the air pressures or quantities of remaining air for each of the wearers, and the controller 204 may respond by displaying visual indicia on the display screen 120 indicating such information. The operator may also be configured to customize the default settings of the thermal imaging camera 104 that affects which information is shown (e.g., the operator may modify the prioritization settings), how the information is presented as visual indicia, and/or the times and durations that the information is presented on the display screen 120.

The thermal imaging camera 104 may selectively present and remove visual indicia representative of the operating status of one or more wearers to prevent oversaturating the operator with information. In a first mode, the thermal imaging camera 104 may display visual indicia representing certain operating status information at all times, unless a specific user request prompts the camera 104 to dim or hide the information. Such information may include an identification of the wearer (e.g., Jones), an air status, a wearer condition alarm state, or the like. In a second mode, the thermal imaging camera 104 is configured to only show visual indicia representing certain operating status information if the operating status information is at an alarm or alert level. Thus, a movement status of the wearer Smith shown in FIG. 8 may not be displayed on the display screen 120 until Smith has been stationary for longer than a threshold period of time, triggering an alarm state. At which time, the controller 204 may generate a display message that includes visual indicia to notify the operator that Smith has been stationary for the last three minutes, for example, and may be incapacitated.

The thermal imaging camera 104 is configured to generate the display messages in consideration of user commands received from the operator. For example, in normal operating conditions, the display message may show the graphical representations of the wearers as well as the graphical representations of other objects (e.g., furniture, walls, etc.) in the thermal image 210 of the surrounding environment in multiple colors based on the relative heat that is radiated from the various objects and wearers. In one embodiment, in response to a user command to "show status" or "show team," the controller 204 is configured to generate a display message that dims, greys, or otherwise de-emphasizes the objects in the surrounding environment while emphasizing the graphical representations of the wearers in the thermal image 210 and displaying various visual indicia associated with each of the graphical representations. The visual indicia provide the operating status of the wearers. The graphical representations of the wearers in the thermal image 210 may be shown in the same color or different colors to distinguish the wearers from one another in the image 210. For example, the background objects may be shown in a uniform light grey color, while the graphical representation associated with Smith is shown in red, the graphical representation associated with Thomson is shown in blue, and the graphical representation associated with Jones is shown in yellow. In another example, in response to a user command to "show Thomson" or "where is Thomson," the controller 204 is configured to generate a display message that dims, greys, or otherwise de-emphasizes everything in the graphical image 210 other than the graphical representation associated with Thomson to allow the operator to immediately locate Thomson in the surrounding environment. The visual indicia on the display message may also provide location information regarding Thomson, such as by presenting that Thomson is "50 feet ahead." In an embodiment, the thermal imaging camera 104 may allow the operator to view Thomson (or another wearer) even if Thomson is behind a wall or another object, since the IR pulses may penetrate some objects that visible light is not able to penetrate.

In an embodiment, the thermal imaging camera 104 may be configured to monitor and track the receipt of status messages from the signaling devices 102 in the surrounding environment of the thermal imaging camera 104. For example, the thermal imaging camera 104 may be configured to detect that an updated status message from a certain signaling device 102 has not been received in an anticipated time window. In response to detecting the signaling devices 102 of one of the wearers are unaccounted for, the thermal imaging camera 104 may take responsive action. For example, the thermal imaging camera 104 may generate a display message that provides visual indicia indicating to the operator that a certain one of the wearers is unaccounted for. Furthermore, the thermal imaging camera 104 may attempt to communicate with the signaling devices 102 of the wearer using the communication circuit 210 (shown in FIG. 6). The thermal imaging camera 104 may also be able to remotely initiate the PASS system or another alarm system on the wearer that is unaccounted for. In addition, or alternatively, the thermal imaging camera 104 may communicate with other signaling devices 102, other thermal imaging cameras 104, and/or remote locations to transmit a message indicating that "Jones is unaccounted for" or "no status from Jones in 3 minutes," for example.

FIG. 9 illustrates a preferred embodiment of an interior view of a mask 900 configured to be worn by a first responder. The mask 900 includes a respirator 902 and a face shield 904. The mask 900 may be donned by the operator of the thermal imaging camera 104. In the illustrated embodiment, the mask 900 is integrated with the thermal imaging camera 104 such that the display screen 120 of the thermal imaging camera 104 is mounted within the mask, such as without limitation, a heads-up display (HUD), in-mask lens, or the like on the face shield 904. Thus, for example, the display screen 120 is a head-up display (HUD) allows the operator to view the display screen 120 without looking down to a handheld device. The HUD 120 also frees the operator from the requirement of carrying a handheld device, such that the operator is able to use his or her hand for other tasks, such as crawling, lifting objects, climbing, and the like. The HUD 120 may be small enough to allow the operator an unobstructed visual view of the surrounding environment through the shield 904. In an embodiment, the IR detector 200 (shown in FIG. 6) of the thermal imaging camera 104 may be disposed in a housing 906 that is mounted on a top 908 of the mask 900. Since the IR detector 200 is mounted on the mask 900, the IR detector 200 is able to detect IR radiation in at least the field of view of the operator. The housing 906 optionally may also contain at least some of the other components of the thermal imaging camera 104, such as the controller 204, the memory 206, and/or the communication circuit 210. In an embodiment, the communication circuit 210 may be configured to transmit initialization messages to any portable signaling devices 102 that are in the field of view of the operator based on the direction that the operator is facing. In another embodiment, the housing 906 may be mounted on a helmet (not shown) of the operator instead of on the top 908 of the mask 900. In an embodiment, the thermal imaging camera 104 further includes a microphone 910 that is a user input device. The microphone 910 receives voice commands from the operator that are used by the controller 204 to generate the display message that is presented on the HUD 120. These display messages include, without limitation, identification of team members, air supply, heart rate, and other biometric, equipment and/or environmental data, including processed logic for situational awareness indicators, such as impending flashover and other like information processing indicating dangers in consideration of merged or fused data inputs regardless of source. In a preferred embodiment the display messages are configurable by the operator to present preferred display message information and/or display message formatting. Preferred display message information includes variations of environmental displays such as temperature, biometric display, and the like, as well as changes in the information to represent changes in set parameters. Preferred display message formatting includes changes in fonts, symbols, colors, timing of the display of the information, location within the display, animations, and the like. The system user may toggle to different displays, eliminate displays, add displays and the like to conform to the user's preferred information flow. In a preferred embodiment different displays can be used for different team members. In a most preferred embodiment alert or emergency notification overrides user preferences and is displayed. Advantages of using a mask version of the invention includes a hands free device and/or passive alert mode notifications for continuous monitoring by connecting the messaging to the user's field of view for warning, alerts, commands and escape messaging. In one embodiment, the addition of an eye-tracking sensor provides control of the system.

EXAMPLE 1

Signal lights (visible and/or IR diodes) are placed on an SCBA pak that are detectable from both a standing and crawling position (2 sets). The signal lights flash to help identify the position of the fireman. Motion detectors in the pak sense when the fireman is stopping by the signal lights changing from a flashing to a solid illumination, or indicating the fireman moving left or right with the appropriate lights being flashed in that direction. Additionally the signal lights indicate a PASS alarm state where they rapidly cycle to identify a downed fireman. Additional sensors in the system identify other modes of motion, such as standing, sitting, etc. with additional signal light flashing status. As such the firefighting team that is entering or exiting a fire in single-file are provided with an effortless visual communication relative to the wearer to those following.

EXAMPLE 2

Multiple signal lights (IR diodes) are placed on different parts of a firefighter's outfit, including on the SCBA pak, the firefighter's helmet, the firefighter's knee (front and back) and the firefighter's boots. Each signal light has unique signal sequences that are detectable by a thermal imaging camera. Once the signal sequences are detected, the signals are processed to relate the unique signal sequence to the location of the signal light on the firefighter and further processed, individually and/or collectively to provide detailed information regarding that firefighter. Processing individual signal sequences provides the status of the firefighter for air tank pressure, PASS alarm, etc. Processing the signal sequences for multiple signal lights relative to each other ("collective interrogation") allows for complex signal communication data and current data on the position and/or orientation of the firefighter which is then used in a virtual representation to team members to show the firefighter's position.

EXAMPLE 3

A team of firefighters has equipment as disclosed in Example 2. The team has thermal imaging viewing through a HUD that has a standard setting for the display of merged infrared image of user, environmental and system status. The team leader changes the display from the displayed thermal information being displayed continuously to flashing on her HUD for 5 seconds every 30 seconds, with a default display of continuous flashing of the displayed thermal information once a team member's air supply is below 30% or biometric readings are outside of commonly understood set parameters. Additionally the team leader knows one of her team members has just completed service on a prior fire call, she sets that team member's biometric parameter for warning indication to a narrower range.

Although one or more embodiments described herein use the thermal imaging system 100 (shown in FIGS. 1 and 6) in an emergency situation, such as in a burning building, where visibility is low, the thermal imaging system 100 is not limited to such emergency situations and environments. For example, the thermal imaging system 100 may also be used in conjunction with security purposes. The wearer wearing a portable signaling device 102 (shown in FIG. 1) may be a security guard that is walking through or around a building or compound that is being secured. The thermal imaging camera 104 may be mounted on the building or around the compound. As the security guard with the signaling device 102 walks within the "line of sight" (meaning the IR detection range) of the thermal imaging camera 104, a message emitted from the signaling device 102 may be detected by the thermal imaging camera 104. The message may provide an operating status of the security guard, and may be conveyed via one or more IR pulse sequences. The operating status may include various information, including an identity of the security guard, movement characteristics of the security guard, a condition of the security guard, and the like. The thermal imaging system 100 may also be used in other applications, whether or not visibility is reduced. In general the information provided with the emitted IR signals are interpreted to complement situational awareness analysis of the members of a team in the environment for operational efficiency and personal and team security.

It should be noted that the various embodiments of the thermal imaging system 100 (shown in FIGS. 1 and 6), or portions thereof, may be implemented in hardware, software or a combination thereof. For example, the various processing units, such as the processors, controllers, and microprocessors described herein may be implemented as part of one or more computers or processors. The processing units may include Random Access Memory (RAM) and Read Only Memory (ROM). The processing units may further each include a storage device, which may be a hard disk drive or a removable storage drive such as a solid state drive, optical disk drive, and the like. The storage device may also be other similar means for loading computer programs or other instructions into the associated processing units. The processing units may be configured to execute a set of instructions that are stored in one or more storage elements, in order to process input data. The set of instructions may include various commands that instruct the processing unit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A thermal imaging system comprising:
an infrared (IR) detector configured to detect ambient IR radiation in a surrounding environment of the IR detector, the IR detector further configured to detect pulse sequences of mechanically-generated IR radiation in a status message emitted by a portable signaling device mounted on a wearer in or around the surrounding environment, the status message representing an operating status of the wearer; and
one or more processors operably connected to the IR detector, the one or more processors configured to analyze the one or more pulse sequences in the status message and generate a display message based on the one or more pulse sequences, the one or more processors configured to convey the display message to a display screen that presents the display message for viewing by an operator of the thermal imaging system, the display message being presented as visual indicia representative of the operating status of the wearer, the visual indicia displayed concurrently with a graphical image of the surrounding environment that is based on the ambient IR radiation detected by the IR detector.

2. The thermal imaging system of claim 1, wherein the IR detector and the one or more processors are configured to be disposed in a housing that is at least one of coupled to a mask worn by the operator or handheld by the operator.

3. The thermal imaging system of claim 1, wherein the operating status of the wearer includes at least one of a health condition of the wearer, an equipment condition of equipment worn by the wearer, a wearer movement status, a wearer location, a wearer orientation, or a wearer identifier.

4. The thermal imaging system of claim 3, wherein the operating status of the wearer includes the health condition and the equipment condition, the health condition including at least one of a temperature of the air surrounding the wearer or a heart rate of the wearer, the equipment condition including a remaining air quantity of an air supply tank worn by the wearer.

5. The thermal imaging system of claim 1, wherein the visual indicia includes at least one of words, numbers, objects, or symbols, the visual indicia being displayed on the display screen at least proximate to a graphical representation of the wearer in the graphical image on the display screen to associate the visual indicia with the graphical representation of the wearer.

6. The thermal imaging system of claim 1, wherein the portable signaling device mounted on the wearer that transmits the status message is a first portable signaling device mounted on a first wearer, the IR detector configured to detect pulse sequences of mechanically-generated IR radiation in a status message emitted by a second portable signaling device mounted on a second wearer that is in or around the surrounding environment, the one or more processors configured to generate the display message that includes first visual indicia representative of the operating status of the first wearer and second visual indicia representative of the operating status of the second wearer.

7. The thermal imaging system of claim 1, further comprising a user input device operably connected to the one or more processors, the user input device configured to receive a user command submitted by the operator of the thermal imaging system, the one or more processors configured to generate the display message to include visual indicia associated with one or more specific portions of the operating status of the wearer identified in the user command.

8. The thermal imaging system of claim 1, wherein the IR detector is configured to detect the mechanically-generated IR radiation emitted by the portable signaling device within a field of view of the IR detector, the first of view of the IR detector being greater than a line of sight of the operator of the thermal imaging system.

9. The thermal imaging system of claim 1, further comprising a communication circuit operably connected to the one or more processors, wherein, prior to receiving the IR radiation from the portable signaling device, the communication circuit is configured to transmit an initialization message to the portable signaling device that requests the portable signaling device to initiate the generation of the pulse sequences of IR radiation.

10. The thermal imaging system of claim 1, wherein the pulse sequences of mechanically-generated IR radiation include multiple pulses of radiation, the one or more processors configured to analyze the pulse sequences to interpret the status message based on at least one of an electrical frequency of each of the pulses, a voltage of each of the pulses, a duration of each of the pulses, or a duration of each pause between consecutive pulses.

11. The thermal imaging system of claim 1, wherein the operating status of the wearer in the status message includes a state of the wearer as one of a pre-alarm state, an alarm state, or a non-alarm state, the one or more processors generating the display message such that the visual indicia indicates the state of the wearer on the display screen.

12. The thermal imaging system of claim 1, wherein the status message representative of the operating status of the wearer that is received by the IR detector includes a set of information related to the operating status, the one or more processors configured to prioritize the set of information and generate the display message such that a first subset of the information having a higher priority is presented as the visual indicia on the display screen and a second subset of the information having a lower priority than the first subset is not presented as the visual indicia on the display screen.

13. The thermal imaging system of claim 1, wherein the one or more processors are configured to generate updated display messages to present visual indicia representative of an updated operating status of the wearer at least one of periodically at a regular interval, responsive to receiving an updated status message from the portable signaling device, responsive to the operating status of the wearer indicating an alarm state, or responsive to receiving a request to display the operating status of the wearer by the operator of the thermal imaging system.

14. A thermal imaging system comprising:
an infrared (IR) detector configured to detect ambient IR radiation in a surrounding environment of the IR detector, the IR detector further configured to detect pulse sequences of mechanically-generated IR radiation in a status message emitted by a portable signaling device mounted on a wearer in or around the surrounding environment, the status message representing an operating status of the wearer;
one or more processors operably connected to the IR detector, the one or more processors configured to analyze the one or more pulse sequences in the status message and generate a display message based on the one or more pulse sequences; and
a display screen operably connected to the one or more processors, the display screen configured to present the display message for viewing by an operator of the thermal imaging system, the display message being presented as visual indicia representative of the operating status of the wearer displayed concurrently with a graphical image of the surrounding environment that is based on the ambient IR radiation detected by the IR detector.

15. The thermal imaging system of claim 14, wherein the IR detector is configured to receive pulse sequences of IR radiation from multiple portable signaling devices mounted on the wearer, the one or more processors configured to analyze the pulse sequences received from the multiple portable signaling devices to determine an orientation of the wearer.

16. The thermal imaging system of claim 14, wherein the visual indicia includes at least one of words, numbers, objects, or symbols, the visual indicia being displayed on the display screen at least proximate to a graphical representation of the wearer in the graphical image on the display screen to associate the visual indicia with the graphical representation of the wearer.

17. The thermal imaging system of claim 16, wherein the visual indicia at least one of identifies the wearer, provides an orientation of the wearer, or provides a movement status of the wearer, provides an equipment condition of equipment worn by the wearer, or provides a health condition of the wearer.

18. The thermal imaging system of claim 14, wherein the one or more processors are configured to generate updated display messages to present visual indicia representative of an updated operating status of the wearer at least one of periodically at a regular interval, responsive to receiving an updated status message from the portable signaling device, responsive to the operating status of the wearer indicating an alarm state, or responsive to receiving a request to display the operating status of the wearer by the operator of the thermal imaging system.

19. The thermal imaging system of claim 14, wherein the status message representative of the operating status of the wearer that is received by the IR detector includes a set of information related to the operating status, the one or more processors configured to prioritize the set of information and generate the display message such that a first subset of the information having a higher priority is presented as the visual indicia on the display screen and a second subset of the information having a lower priority than the first subset is not presented as the visual indicia on the display screen.

20. The thermal imaging system of claim 14, further comprising a user input device operably connected to the one or more processors, the user input device configured to receive a user command submitted by the operator of the thermal imaging system, the one or more processors configured to generate the display message to include visual indicia associated with one or more specific portions of the operating status of the wearer identified in the user command.

* * * * *